United States Patent [19]

Firestone et al.

[11] 4,086,423
[45] Apr. 25, 1978

[54] PROCESS FOR CEPHEM SYNTHESIS

[75] Inventors: Raymond A. Firestone, Fanwood; Ronald W. Ratcliffe, N. Plainfield; Burton G. Christensen, Scotch Plains, all of N.J.

[73] Assignee: Merck & Co., Inc., Rahway, N.J.

[21] Appl. No.: 624,369

[22] Filed: Oct. 21, 1975

Related U.S. Application Data

[63] Continuation of Ser. No. 406,000, Oct. 12, 1973, abandoned.

[51] Int. Cl.$^2$ ............................................. C07D 501/08
[52] U.S. Cl. ........................................ 544/21; 544/16; 544/22; 544/24; 544/25; 544/26; 544/27; 544/28; 544/29; 544/30
[58] Field of Search .................... 260/243 C; 424/246; 544/16, 21, 22, 23, 24, 25, 26, 27, 28, 29, 30

[56] References Cited

U.S. PATENT DOCUMENTS

| | | | |
|---|---|---|---|
| 3,534,029 | 10/1970 | Beyerman | 260/243 |
| 3,962,224 | 6/1976 | Christensen et al. | 260/243 C |
| 3,987,040 | 10/1976 | Cheng et al. | 260/243 C |

FOREIGN PATENT DOCUMENTS

| | | |
|---|---|---|
| 2,318,829 | 10/1973 | Germany. |

OTHER PUBLICATIONS

Ratcliffe et al., Tetrahedron Letters, 1973, No. 46, pp. 4643–4646.

*Primary Examiner*—Donald G. Daus
*Assistant Examiner*—Diana G. Rivers
*Attorney, Agent, or Firm*—James A. Arno; Julian S. Levitt

[57] ABSTRACT

Cephalosporin antibiotics of the formula:

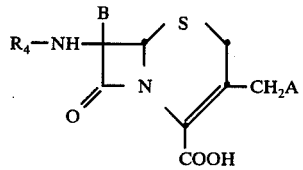

are produced by cycloaddition of a glycine derivative of the formula

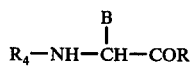

with a thiazine derivative of the formula

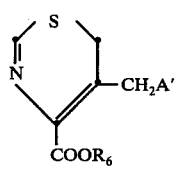

2 Claims, No Drawings

PROCESS FOR CEPHEM SYNTHESIS

This is a continuation of application Ser. No. 406,000 filed Oct. 12, 1973 (now abandoned).

This invention relates to a novel method for the total synthesis of cephalosporin antibiotics which find utility in human and veterinary medicine.

The cephalosporins are valuable antibiotic substances useful in the treatment of pathogenic infections in humans ans animals in addition to possessing utility for a variety of industrial applications. These products can be prepared from cephalosporins such as cephalosporin C and 7α-methoxy-7β-(D-5-amino-5-carboxyvaleramido)-3-carbamoyloxymethyl-3-cephem-4-carboxylic acid which are recovered from fermentation broths produced by growing suitable strains of microorganisms. For example, cephalothin can be prepared from cephalosporin C by replacing the aminoadipoyl side chain with a 2-thienylacetyl group. However, these processes for the preparation of cephalosporins suffer from several disadvantages. In the first place, the yields of cephalosporins obtained by fermentation are low, and the replacement of the aminoadipoyl group involves a number of steps which are difficult to carry out on a commercial scale. Other processes for preparing cephalosporins starting with the penicillin nucleus and synthetic methods are also known in the art. However, these processes likewise are difficult to carry out on a commercial scale and result in obtaining only low yields of the desired products. Accordingly, other methods suitable for the preparation of cephalosporin compounds on a large scale have been sought by many workers in this art.

In accordance with this invention it has now been found that the total synthesis of cephalosporin antibiotics may be effected by a cycloaddition approach employing glycine derivatives and thiazine moieties.

The process of the invention for the preparation of useful cephalosporins is as follows:

FLOWSHEET I

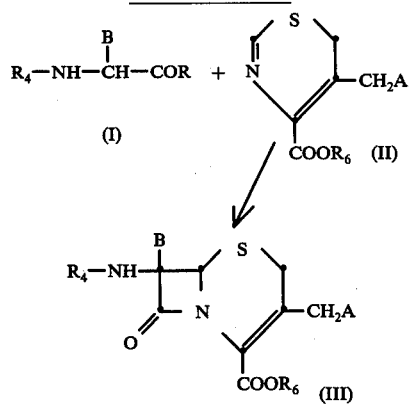

wherein:

B is H, $CH_3$, SR', or $OCH_3$; wherein R' is lower alkyl of 1-6 carbon atoms (e.g. methyl, ethyl, propyl, butyl, pentyl, etc.) or aryl (e.g. phenyl and the like); A represents hydrogen, a protected hydroxy, halo, a protected mercapto, acyloxy, acylthio, substituted hydroxy, substituted mercapto, an azido, cyano, a protected amino, or N-substituted amino, or a 5-membered heterocyclic thio group having 1-4 hetero atoms, the latter being S, O or N; $R_6$ is a carboxy-blocking group; R is halogen (Cl, Br, F, I), $-O-COO-R_6$, $-OR_6$, trifluoromethanesulfonate, $N_3$, $OCOCF_3$ or CN; $R_4$ is a carboxylic acyl group or a radical capable of conversion to such group.

In the foregoing flowsheet the starting compound an acylated glycine (I) is condensed with a 6H-1,3 thiazine (II) in the presence of a base, preferably an organic base such as triethylamine, pyridine, etc. to produce the corresponding cephalosporin (III). The reaction may be effected at temperatures which may vary from −100° to +50°, temperatures of the order of −78° to 0° C being preferred. Solvents that may be utilized in the practice of the invention include $CH_2Cl_2$, $CHCl_3$, $CCl_4$, benzene, tetrahydrofuran, ethyl acetate, pyridine or ethyl ether.

If desired, the protective group ($R_6$) on the carboxy function may be cleaved to produce the free acid of (III).

The cleavage of the protective groups on the carboxy function is accomplished in accordance with procedures well known in this art. Thus, for example, the trichloroethoxycarbonyl group is removed by reaction with zinc and acetic acid, and the t-butoxycarbonyl and benzhydryl groups are removed by reaction with trifluoroacetic acid.

Also within the scope of the invention are the reaction of glycine derivatives and thiazine moieties wherein the cephalosporins produced thereby are further converted to useful cephalosporin via techniques well known in the art. Illustrative of the above is the following:

(A) Reaction of a diacylglycine derivative with a thiazine resulting in the production of a diacylamido cephalosporin followed by cleavage of the 7-diacylamido cephalosporin to produce useful 7-monoacylamido cephalosporins compounds in accordance with the teachings of Belgium Pat. No. 768,528 which are incorporated herein by reference. Alternatively the 7-diacylamide cephalosporin may be cleaved to produce a 7-amino cephalosporin which may be acylated in accordance with techniques well known to the art.

Acylation of the 7-amino cephalosporins to produce the 7-acylamido cephalosporins may be accomplished by employing acylating agents such as an acyl halide or acyl anhydride such as an aliphatic, aromatic, heterocyclic, aralphatic or heterocyclic aliphatic carboxylic acid halide or anhydride. Other acylating agents may also be employed, for example, a mixed acid anhydride with other carboxylic acids and particularly lower alkyl esters of carboxylic acids; also, carboxylic acids in the presence of a carbodiimide such as 1,3-dicyclohexylcarbodiimide, an activated ester of a carboxylic acid such as the p-nitrophenyl ester or by enzymatic acylation. The reaction may be conducted at a temperature in the range of from about −20° C. to about 100° C. but is preferably conducted at a temperature in the range of from 0° to 25° C. Any solvent in which the reactants are soluble and substantially inert may be employed, for example, hydrocarbons such as benzene, toluene, and the like, $CH_2Cl_2$, $CHCl_3$, or tertiary amines, for example, trialkylamines and heterocyclic amines such as triethylamine, pyridine and the like. The reaction is conducted for a period of time of from about five minutes to a maximum of three hours but, in general, a reaction time of about 0.05 to about one hour is sufficient.

Representative of the diacylglycine derivatives that may be employed in the practice of the invention include:

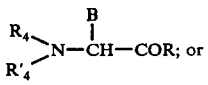

cyclic moieties such as

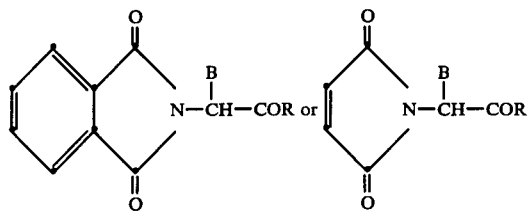

Flow Sheet II is illustrative of the reaction involving a diacyglycine.

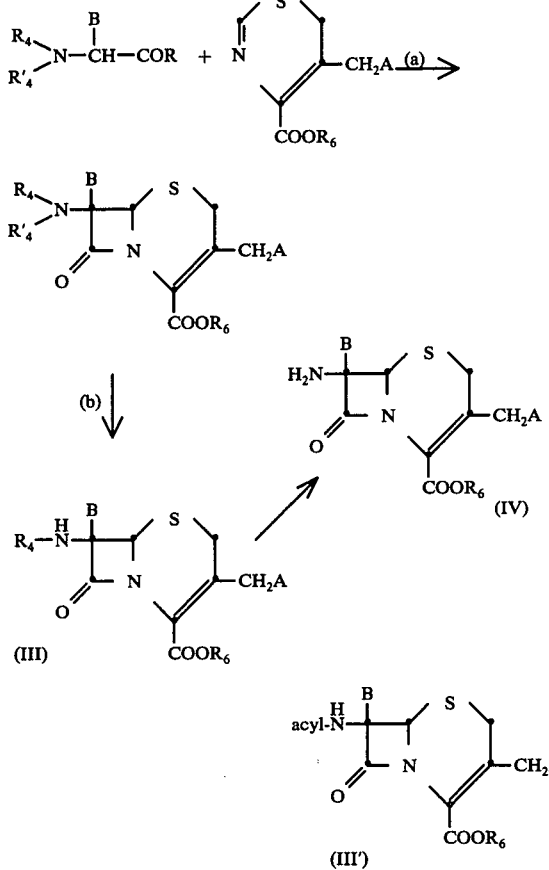

wherein R, A, $R_6$, B, $R_4$ is as set forth above and $R_4'$ is an acyl group corresponding to $R_4$.

The reaction (a) of the diacylated glycine and thiazine occurs under conditions similar to that set forth above (Flow Sheet I) where a monoacylglycine is reacted with a thiazine to form the cephalosporin.

The step of cleaving (b) the acyl group $R_4$ can be effected in several ways, namely, by prolonging the reaction time, by the addition of an alcohol such as a loweralkanol or a loweralkyl thiol or by hydrolysis in an aqueous solution containing a small amount of an acid or a base. Thus, in some cases cleavage is effected by the addition of a loweralkanol or loweralkyl thiol containing from 1-6 carbon atoms, and aralkanol such as benzyl alcohol or the corresponding thiol. In addition prolonged heating of the reaction mixture can result in the cleavage of the acyl group and the preparation of the desired useful 7-acylated cephalosporin compound.

It may be noted that the cleavage of the diacylated product is also effected by reacting the material with a silyl halide such as trimethylsilyl chloride. This process is readily carried out by heating the trimethylsilyl chloride with the imide in a suitable non-reactive solvent such as ethylene dichloride at about 60° C. for about 1 hour. The desired monoacylated cephalosporin compound is then recovered from the reaction mixture in accordance with procedures known in this art.

Where $R_4$ and $R_4'$ are different and one is more labile than the other, the more labile acyl group can be removed selectively in a stepwise manner in accordance with the above resulting in the preparation of the monoacyl cephalosporin (III).

If desired, the monoacyl cephalosporin (III) may be further cleaved to produce the 7-aminocephalosporin which is then acylated in accordance with procedures set forth above to produce useful cephalosporin antibiotics (III).

In the case of cyclic diacyl moieties, cleavage may be effected utilizing hydrazine.

(B)) Reaction of an iminoglycine derivative with a thiazine to form a 7-imino cephalosporin which is then removed and the cephalosporin treated with an acylating agent as described above to yield useful 7-acylamino cephalosporins in accordance with the teachings of U.S. Ser. No. 277,464, filed Aug. 2, 1972 in the names of Christensen and Cama which are incorporated herein by reference.

The iminoglycines of the invention may be prepared by reacting a suitable aldehyde or ketone with the amino group. Particularly preferred are aromatic aldehydes, substituted or unsubstituted, having 1, 2, or 3 aromatic rings, such as those derived from benzene or naphthalene. One or more substituents are possible in the aromatic aldehyde, including $C_1$ to $C_3$ alkyl (e.g., methyl, ethyl, propyl, isopropyl), $C_1$ to $C_3$ alkoxy (e.g., methoxy, ethoxy, propoxy, etc.), cyano, nitro, halogen (e.g. chlorine, fluorine, bromine, or iodine), trifluoromethyl, $C_1$ to $C_4$ carboxyalkyl (e.g., carboxymethyl, carboxyl ethyl, etc.), sulfonyl, and carboxy derivatives such as esters, amides or the like.

Representative of the above aromatic aldehydes are benzaldehyde, naphthaldehyde, salicylaldehyde, m-tolualdehyde, o-tolualdehyde, o-chlorobenzaldehyde, o-methoxybenzaldehyde, p-nitrobenzaldehyde, p-chlorobenzaldehyde, m-hydroxybenzaldehyde, 2-hydroxynaphthaldehyde, as well as others.

Also suitable are aliphatic aldehydes, or ketones including those having 1-10 carbon atoms as well as substituted aliphatic aldehydes and ketones; the optional substituents can be those mentioned in discussing the aromatic aldehydes. Representative are acetone, hexafluoroacetone, chloral, ethoxyacetaldehyde and others.

The iminoglycines may be prepared by treating the $K^+$ or $(butyl)_4 N^+$ salt of glycine with the appropriate aldehyde in solvent systems such as EtOH or N,N-dimethylformamide. Alternatively, the iminoglycine may be produced by treating methyl or ethyl glycinate with an aldehyde in EtOH or CHCl₃/MgSO₄ and the like followed by saponification of the ester. Activation of the iminoglycines may be effected utilizing either oxalyl chloride or isobutoxycarbonyl chloride and triethyl amine.

Flow Sheet III is illustrative of the reaction involving an iminoglycine derivative:

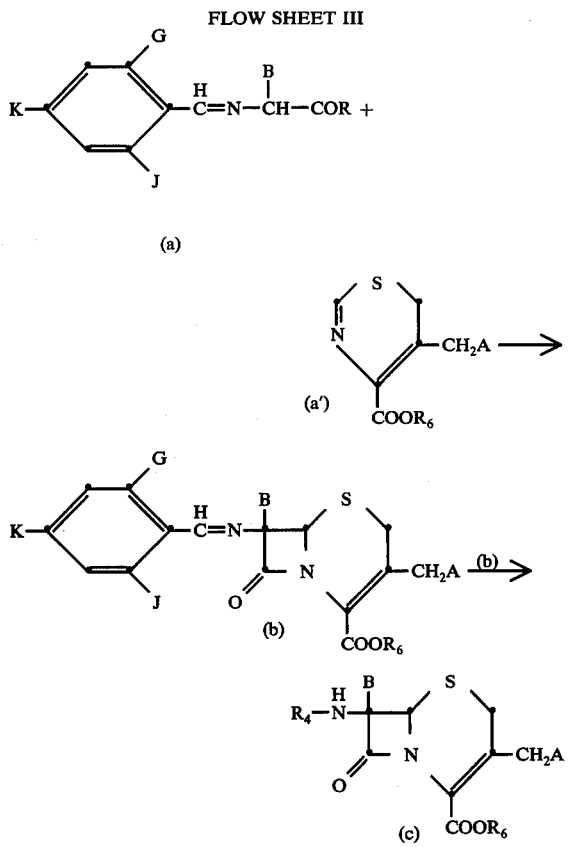

wherein B, R, A, R₆, R₄ is as set forth above and J, G, or K each independently is nitro, methylsulfonyl, halo, cyano, hydrogen, or the like.

The reaction of the iminoglycine derivative (a) and thiazine (a') occurs under conditions similar to that set forth above (Flow Sheet I) where a monoacyglycine is reacted with a thiazine to form the cephalosporin.

Compound (b) is directly acylated to the desired 7-acylamino compound (c) by reaction with molecular excess of an acyl halide or acyl anhydride. The acyl halides can be, for instance, phenylacetyl chloride, furylacetyl chloride, thienylacetyl chloride, α-carboxyphenylacetylchloride, α-carboxy-thienylacetyl chloride and the like. When carboxy, OH or NH₂ groups are present in the acyl halide, such as the α-carboxyphenylacetylchloride, these groups are blocked using, e.g., a benzyl or benzhydryl substituent which can be easily removed later. The reaction is conducted in an inert solvent in the presence of an optional metal catalyst and at a temperature can be from about −20° C. to 20° C. The final product is isolated by standard procedures, most suitably preparative thin-layer chromatography or column chromatography.

In the acylation reaction, it has been found that the optional process utilizes a metal catalyst. The process proceeds best when conducted in two steps. The first step utilizes the catalyst in solvent. The Schiff's base is dissolved in an inert polar solvent, such as tetrahydrofuran, dimethylsulfoxide, dioxane, dimethylformamide, methanol, ethanol, methylene chloride, or chloroform. A small additional amount of water is then added; a volume such that the solvent to water volume:volume ratio is about 5-6:1. Then the metal catalyst is added. This catalyst can be described as $ML_n$ wherein M is a metal such as palladium, platinum, nickel, ruthenium, rhodium, cobalt, or iron; and L is a ligand such as halo; carbonyl (—CO—); cyclopentadienyl ($\pi C_5H_5$); phenylcyano (Ph—C≡N); and $n$ is an integer such that the valence requirements are satisfied. More preferably, the metal is palladium or platinum, and L is halogen, preferably chloride. The most preferred catalyst is palladium chloride ($PdCl_2$). The amount of catalyst needed is from one-half to 1 molar equivalents of the amount of the Schiff's base in the reaction, although a small excess can also be used.

The reaction mixture is then stirred at ambient temperature for 1–5 hours. The solvent is then removed at reduced pressure. After trituration with petroleum ether or a similar inert solvent, a crystallizable residue is recovered which is a complex of the metal and the amino-containing cephalosporin. This residue is then dissolved in a polar solvent, such as methylene chloride, chloroform, ethyl acetate, or diethylether, and cooled to about 0°–15° C. An excess of an organic base, such as pyridine, triethylamine, triisopropylamine, or the like is then added, followed by the addition of an approximately equimolar amount of the desired acyl halide or acyl anhydride. The reaction mixture is stirred at the low temperature for another 10–20 minutes, then allowed to warm to ambient temperature. The reaction product is then isolated by purification using techniques substantially as described before.

It may be noted that in the process for the total synthesis of useful, antibiotically active cephalosporins (wherein B is hydrogen), the intermediates involved in said process may be further reacted to obtain useful antibiotically active 7-methoxy or 7-methyl cephalosporins as follows:

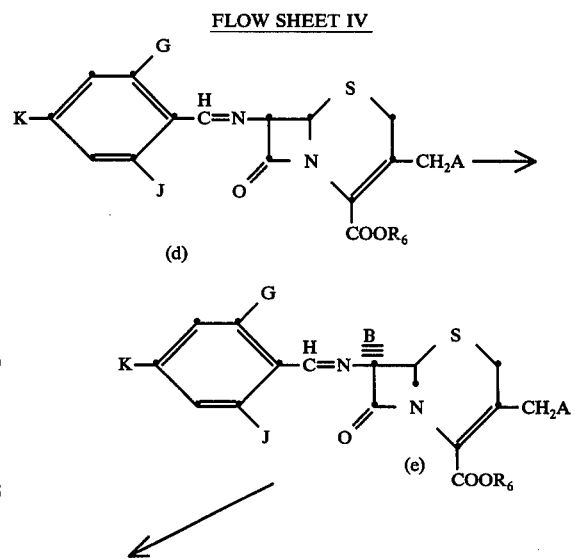

-continued
FLOW SHEET IV

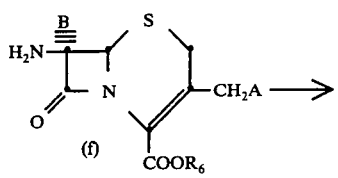

(f)

(g)

The process can be summarized briefly as having three major steps: the first is the substitution of the 7-imino derivative (see Flow Sheet III) with the chosen reactant supplying the B group desired ($CH_3$, SR or $OCH_3$). The specific reactant depends on the identity of the B group. The second step is then the regeneration of the amino group. The third step is the acylation of the amino cephalosporin to produce useful antibiotically active cephalosporins.

The initial reaction involves the substitution of the B group at the carbon atom adjacent to the imino nitrogen. This reaction takes place in the presence of an inert solvent, and in the additional presence of an activating agent which is an organic or inorganic base. Suitable solvents are glyme, dioxane, acetonitrile, dimethylformamide, tetrahydrofuran, dimethylsulfoxide, benzene, toluene, and the like.

The activating agent can be any of a number of organic or inorganic bases. Tertiary (loweralkyl) amines are suitable, such as triethylamine, diisopropyl ethylamine; pyridine is also used. Lithium alkyls and lithium aryls, such as lithium alkyls having 1–4 carbon atoms, e.g., t-butyl lithium or phenyl lithium, could be used. Sodium hydride, lithium amides such as lithium diisopropylamide. LiOMe and potassium t-butoxide are also suitable.

The activating agent is added to the solution of compound (d) at a low temperature ($-100°$ to $0°$ C. and preferably $-100°$ to $-60°$ C.) and under an inert atmosphere. In general one equivalent of activating agent is employed.

The activated compound (d) is not isolated, but the next reagent is added directly to the reaction mixture.

The specific reagent which is employed in the reaction with the activated compound (d) to result in the substitution of the chosen B group obviously depends on the B group desired.

In the case of B = $OCH_3$ the reagent can be dimethyl peroxide, methyl t-butyl peroxide, methylphenylsulfenate, o-methyldimethyl sulfoxonium methosulfate, or N-methoxy pyridinium methosulfate. It may be noted that an alternative method for the introduction of the $OCH_3$ group involves reaction of activated (d) with a halogenating agent such as N-bromosuccinimide followed by methanolysis. Where B = $CH_3$ the following reagents may be employed: methyl sulfate, methyl chloride, methyl bromide and methyl iodide. The following reagents may be employed: phenylsulfenyl halide or lower alkyl disulfide (e.g. methyldisulfide or lower alkyl sulfenyl halides such as methyl sulfenyl chloride.

Once the compound (e) has been prepared, the imino moiety is converted to the amino moiety of compound (f).

The regeneration of (f) from (e) takes place by the reaction of (e) with an amine in the presence of an acid catalyst. The amine employed can be aniline, hydrazine, or hydrazine derivatives such as phenylhydrazine, 2,4-dinitrophenyl hydrazine, and the like. The acid catalyst can be any commonly used strong organic or inorganic acid such as hydrochloric acid or p-toluene sulfonic acid. One preferable combination utilizes aniline hydrochloride, which serves as both acid and amine. Another preferred combination is 2,4-dinitrophenyl hydrazine and p-toluene sulfonic acid. The reaction conditions of the regeneration are chosen such that no undesired hydrolysis or ring damage occurs, and is preferably carried out in a lower alkanol medium (1–5 carbon atoms), such as methanol, ethanol, and the like, although other solvents including dimethoxyethane or dimethyl formamide may also be used. The temperature is that of the surroundings. The relative amounts of acid and amine employed depends on the specific aldehyde and amine used, since the regeneration involves an equilibrium. The choice of amounts of the reagents is within the skill of one in the art.

Compounds (d) and (e) prepared in the reactions can be used to prepare valuable antibacterial agents useful against gram-positive and gram-negative bacteria. When the amino group of compound (f) is acylated via techniques well known to the art, the resulting products (g) have activity against gram-negative organisms.

An alternative procedure by which the 7-imino derivative (see Flow Sheet III) may be converted to useful antibiotically active cephalosporins wherein B is other than H (e.g., $OCH_3$) is as follows:

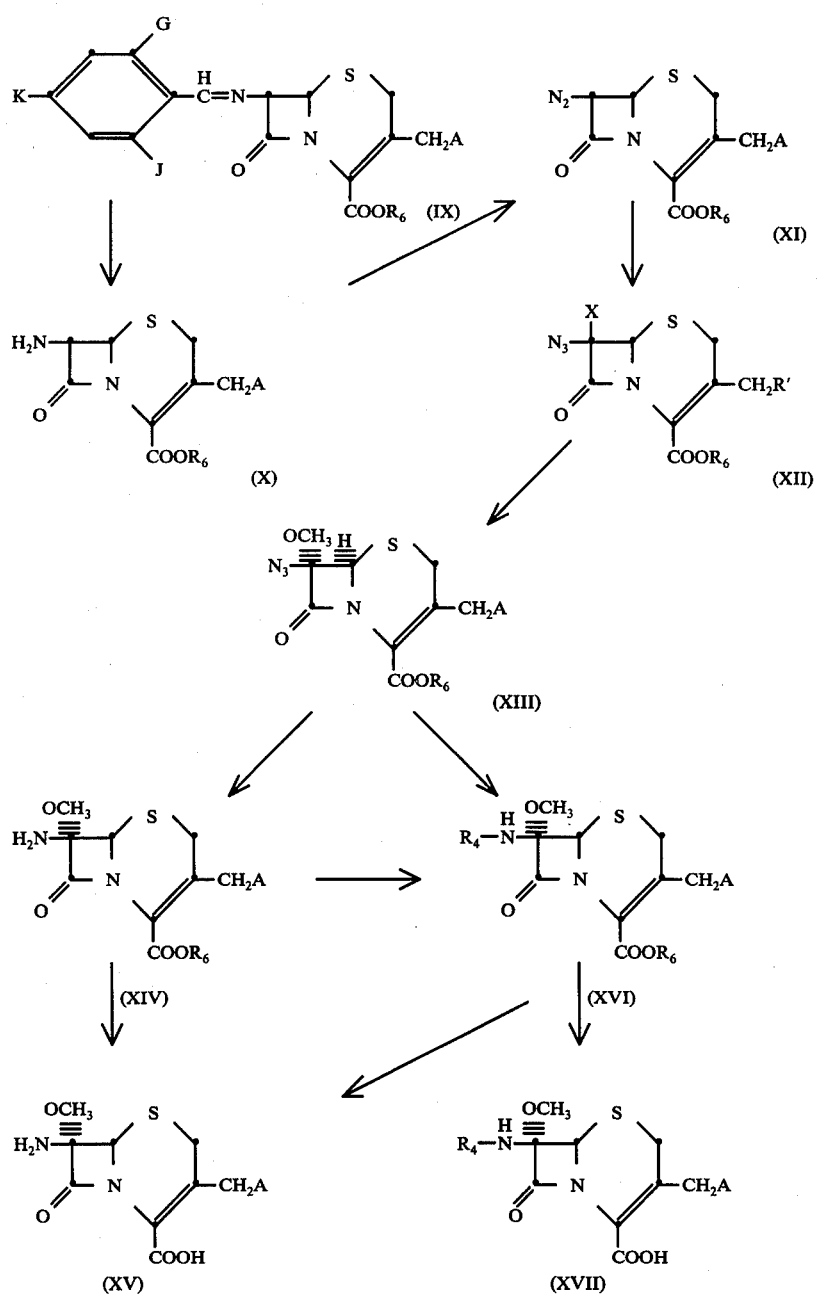

where the substituents are as defined above.

In the above process the imino compound (IX) is converted to the 7-amino cephalosporin (X). The 7-amino compound is converted to the corresponding 7-diazocephalosporin acid ester by reaction with nitrite. The 7-diazocephalosporanic acid ester XI is then reacted with a halo azide from the group consisting of bromine, chlorine or iodine azide, preferably in the presence of a tertiary amine azide, to produce the intermediate 7-halo-azidocephalosporanic acid ester XII which on reaction with a suitable nucleophilic reagent is converted to the desired 7-$OCH_3$-7-azidocephalosporanic acid ester XIII. This intermediate product is reduced and acylated in one step to form the substituted cephalosporanic ester XVI which can then be cleaved to remove the blocking group and obtain the cephalosporanic acid or a salt thereof XVII. Alternatively, as shown in the flowsheet, the 7-$OCH_3$-7-azidocephalosporanic acid ester XIII is reduced to the 7-$OCH_3$-7-aminocephalosporanic acid ester XIV which can be acylated to produce the 7-$OCH_3$-7-acylaminocephalosporanic acid ester XVI. Alternatively, the ester group of compound XIV can be cleaved to obtain the free acid XV which can be acylated to form the desired substituted cephalosporin or a salt thereof. The step of cleaving the blocking group is readily effected in accordance with methods known in this art. For example, an aralkyl group such as the benzyl ester is removed by reduction, a silyl ester can be removed by hydrolysis to form the free acid or a salt thereof and a benzhydryl group is readily cleaved by reaction with trifluoroacetic acid in the presence of anisole. In this process other esters which are readily cleaved to form the free acid such as trichloroethyl, phthalimidomethyl, succinimidomethyl, p-methoxybenzyl, p-nitrobenzyl, phenacyl and t-butyl and the like can be used. Also, the 3-substituent on the $\Delta^3$-cepham nucleus can be varied following the procedures known in this art to obtain the useful cephalosporins.

The diazotization of the 7-amino ester is carried out in accordance with processes well known in this art. Thus, it is conveniently effected in aqueous or aqueous-organic solvent medium, for example by reaction with sodium nitrite in the presence of an acid or by reaction with an organic nitrite.

Examples of such solvents that might be mentioned are methylene chloride, ether, benzene, toluene, chloroform, and the like. The reaction is preferably carried out at temperatures between about 0° and 50° C.; usually it is most conveniently effected at room temperature. The isolation of the desired diazo compound is readily accomplished in accordance with methods known in the art.

The step of producing the halo azide intermediate is carried out by reacting the diazo compound with a halo azide at a temperature between about $-25°$ and 50° C. for sufficient time to complete the formation of the desired compound. The reaction is preferably carried out in a suitable organic solvent medium which is inert to the reactants. Various solvents which do not contain an active hydrogen such as methylene chloride, chloroform, benzene, toluene, ether and the like, or mixtures thereof provide suitable mediums for carrying out the reaction. Generally, it is preferred to effect the reaction in the presence of a second azide such as lithium azide or a tertiary ammonium azide, for example triethylammonium azide, since under these conditions the formation of the undesired di-halo compound is avoided. The halo azide is used in an amount in slight excess of stoichiometric requirements. The amount of second azide is not critical and it is generally desirable to use an excess in order to obtain maximum yields of the desired halo azido compound under optimum conditions. After completion of the formation of the halo azide the product is recovered and can be purified further, for example by chromatography, in accordance with processes well known in this art.

The next step of the process comprising the replacement of the halo substituent by a methoxyl group is effected by reacting the halo azide with a substance capable of furnishing an $OCH_3$ group to replace the halo. This reaction is preferably carried out in the presence of a suitable non-reactant solvent such as methylene chloride, chloroform, benzene, toluene, ether, petroleum ether and the like; again it is desirable to avoid using any solvents containing an active hydrogen. Thus, the nucleophilic displacement reagent can be methanol which results in the displacement of the halo group and the introduction of a methoxy group. The reaction is preferably carried out in the presence of a heavy metal cation such as a silver salt.

In the next step of the above-described process the 7-azido-7-$OCH_3$ compound is then reduced to afford the corresponding 7-amino-7-$OCH_3$ compound. Various methods of carrying out this reduction can be employed, but it is generally preferred to carry out the reduction of the azido to the amino group by catalytic hydrogenation employing a noble metal catalyst such as platinum, palladium or oxides thereof. These processes are carried out in accordance with procedures well known in this art. Alternatively, the reduction can be effected in the presence of a suitable acylating agent to produce the desired 7-acylamido-7-$OCH_3$ compound. The 7-amino compound can be reacted with suitable acylating agents using procedures well known in this art as described hereinafter to obtain the desired 7-acylamido compounds.

The acylation of the 7-amino-cephalosporanic acid compound is readily effected by reaction with an acylating agent such as an acyl halide (chloride or bromide) or a functional equivalent thereof such as an acid anhydride, a mixed acid anhydride with other carboxylic acids and particularly lower aliphatic esters of carboxylic acid, a carboxylic acid in the presence of a carbodiimide such as 1,3-dicyclohexylcarbodiimide, an activated ester and the like, or enzymatic acylation pursuant to acylation methods used for the preparation of cephalosporins which are well known in this art.

In addition to the procedures described above useful cephalosporins may be prepared in accordance with the invention by condensation of an N-protected glycine (eg. t-butoxy carbonyl glycine) and thiazine. The 7-protected amido group of the cephalosporin formed is subsequently deblocked to produce a 7-amino cephalosporin which may then be acylated to form the desired useful cephalosporin.

Examples of groups that may be employed to block or protect the amino group of the glycine are well known in the art. For example, the amino group is most conveniently blocked by a group such as trichloroethoxycarbonyl-p-nitrobenzyloxycarbonyl, t-butoxycarbonyl, benzoylmethoxycarbonyl, trimethylsilyl, p-methoxybenzyloxycarbonyl, o-nitrophenylthio, benzenesulfonyl and coluenesulfonyl.

Other representative blocking groups that may be employed in the practice of the invention include

which is obtained from the reagent

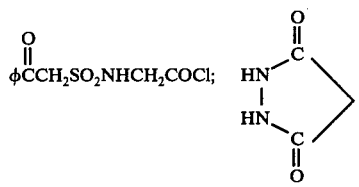

which is obtained from the reagent

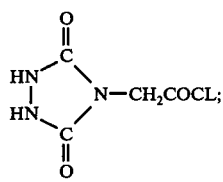

utilizing the reagent OCN—$CH_2$-COCl which affords the blocking group OC, the blocking group

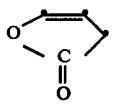

which is obtained via the reagent

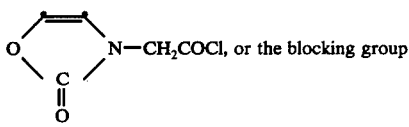, or the blocking group

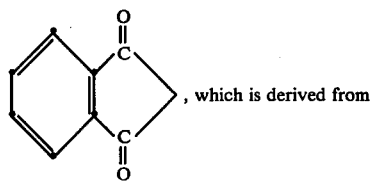, which is derived from

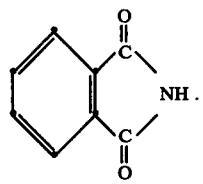

The following scheme is illustrative of the process.

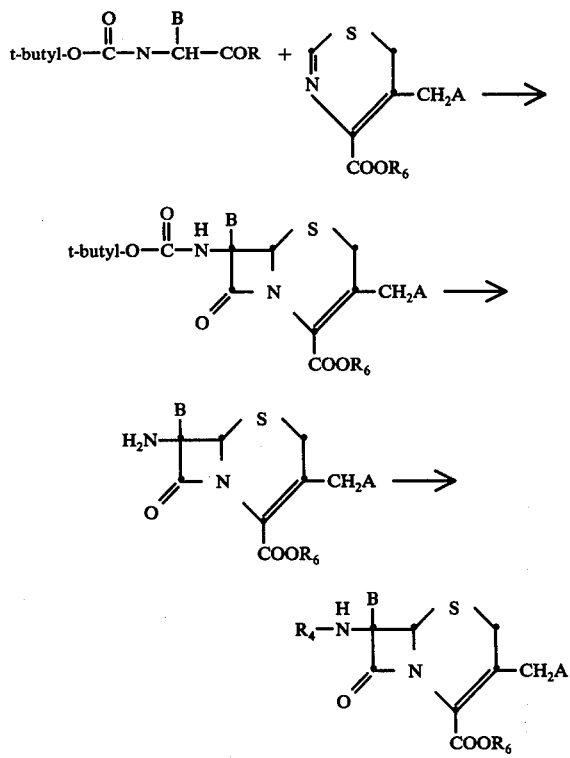

Transformation of the 7-protected amido to the 7-amino cephalosporin may be conveniently effected by treatment with anisole and trifluoroacetic acid or by hydrogenation utilizing palladium catalyst, zinc or HgO. The acylation of the 7-amino cephalosporin may proceed in accordance with techniques well known to the art.

The acyl radical represented by $R_4$ can be a substituted or unsubstituted aliphatic, aromatic or heterocyclic, araliphatic or heterocylylaliphatic carboxylic acid radical or a carbothioic acid radical such as the acyl radicals of the known cephalosporins and penicillins. These acyl radicals can be represented by the general formula $$-CO(CH)_m(CH_2)_nR_3$$
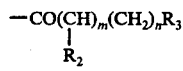

where $R_2$ is a radical of the group defined below, $m$ and $n$ represent 0–4 and $R_3$ represents R″ or ZR″, which are defined below.

One group of acyl radicals can be represented by the acyl group general formula $$-\overset{O}{\underset{\|}{C}}-R''$$

wherein R″ represents a substituted or unsubstituted straight or branched chain alkyl, alkenyl or alkynyl group; aryl, aralkyl; cycloalkyl; or a heteroaryl or heteroaralkyl group. These groups can be unsubstituted or can be substituted by radicals such as alkyl, alkoxy, halo, cyano, carboxy, sulfoamino, carbamoyl, sulfonyl, azido, amino, substituted amino, haloalkyl, carboxyalkyl, carbamoylalkyl, N-substituted carbamoylalkyl, guanidino, N-substituted guanidino, guanidinoalkyl, and the like. Representative examples of such acyl groups that might be mentioned are those wherein R″ is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, $\beta,\beta$-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)-5-methyl-4-isoxazolyl, D-4-amino-4-carboxybutyl, D-4-N-benzoylamino-4-carboxy-n-butyl, p-aminobenzyl, o-aminobenzyl, m-aminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl,-guanidinomethylphenyl, 4-guanidinomethylbenzyl, 4-guanidinobenzyl, 4-guanidinophenyl, 2,6-dimethoxy-4-guanidinophenyl, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl,difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3- (5-methylthienyl)methyl, 2- or 3-(5-methoxythienyl)methyl, 2- or 3- (4-chlorothienyl)-methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, and tetrazolylmethyl.

The acyl group can also be a radical of the formula

wherein $n$ is 0–4, Z represents oxygen or sulfur, and $R''$ is defined as above. Representative members of the substituent

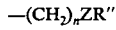

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)phenylthiomethyl, 2-thiazolylthiomethyl, p-(sulfo)phenoxymethyl, p-(sulfo)phenylthiomethyl, p-(carboxy)phenoxymethyl, p-(carboxy)phenylthiomethyl, p-(carboxymethyl)phenoxymethyl, p-(carboxymethyl)phenylthiomethyl, 2-pyrimidinylthiomethyl, phenethylthiomethyl, 1-(5,6,7,8-tetrahydronaphthyl)oxomethyl 6,8-bis(methylthio)octanoyl.

Alternatively, the acyl group can be a radical of the formula

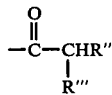

wherein $R''$ is defined as above and $R'''$ is a radical such as amino, hydroxy, azido, carbamoyl, guanidino, acyloxy, halo, lower alkyl, sulfamino, tetrazolyl, sulfo, carboxy, carbalkoxy, and the like. Representative members of the substituent

that might be mentioned are α-aminobenzyl, α-amino-2-thenyl, α-methylaminobenzyl, α-amino-γ-methylmercaptopropyl, α-amino 3- or 4-chlorobenzyl, α-amino-3 or 4-hydroxybenzyl, α-amino-2,4-dichlorobenzyl, α-amino-3,4-dichlorobenzyl, D(—)-α-hydroxybenzyl, α-carboxybenzyl, α-amino-3-thenyl, α-amino-2-thenyl, D-(—)-α-amino-3-chloro-4-hydroxybenzyl, D(—)-α-amino-3-thenyl, 1-aminocyclohexyl, α-(5-tetrazolyl)benzyl, α-sulfaminobenzyl, α-sulfamino-3-thenyl, α-(N-methylsulfamino)-benzyl, D(—)-α-guanidino-2-thenyl, D(—)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-oxadiazolyl)-carboxymethyl, 4-(5-methoxy-1,3-sulfadiazolyl)-aminomethyl, 4-(5-methoxy-1,3-sulfadiazolyl)-hydroxymethyl, 4-(5-methoxy-1,3-sulfadiazolyl)-carboxymethyl, 2-(5-chlorothienyl)-aminomethyl, 2-(5-chlorothienyl)-hydroxymethyl, 2-(5-chlorothienyl)-carboxymethyl, 3-(1,2-thiazolyl)-aminomethyl, 3-(1,2-thiazolyl)-hydroxymethyl, 3-(1,2-thiazolyl)-carboxymethyl, 2-(1,4-thiazolyl)-aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, 2-azidooctyl-3-phenyl-3-azidomethyl, α-sulfobenzyl, and α-phosphonobenzyl. Also of interest is the following acyl moiety:

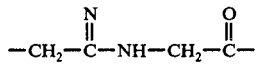

Alternatively, the group

can be a sulfonamido group such as phenysulfonamido, ethylsulfonamido, benzyl sulfonamido, 2,5-dimethylphenylsulfonamido, 4-chlorophenylsulfonamido, 4-chlorophenylsulfonamido, 4-methoxyphenylsulfonamido, and the like.

The acyl substituents of the general formula

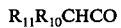

wherein $R_{10}$ and $R_{11}$ are as defined below represent a preferred group of substituents because of their generally useful antibiotic activity. $R_{10}$ represents hydrogen, halo, amino, guanidino, phosphono, hydroxy, tetrazolyl, carboxy, lower alkyl, sulfo or sulfamino. $R_{11}$ represents phenyl, substituted phenyl, a monocyclic heterocyclic 5- or 6-membered ring containing one or more oxygen, sulfur or nitrogen atoms in the ring, substituted heterocycles, phenylthio, phenoxy, heterocyclic or substituted heterocyclic thio groups; or cyano. The substituents can be halo, carboxymethyl, guanidino, guanidinomethyl, carboxamidomethyl, aminomethyl, nitro, methoxy or methyl. Examples of these preferred substituents that might be mentioned are phenylacetyl, phenoxyacetyl, 3-bromophenylacetyl, p-aminomethylphenylacetyl, 4-carboxylmethylphenylacetyl, 4-carboxamidomethylphenylacetyl, 2-furylacetyl, 5-nitrofurylacetyl, 3-furylacetyl, 2-thienylacetyl, 5-chlorothienylacetyl, 5-methoxythienylacetyl, α-guanidino-2-thienylacetyl, 3-thienylacetyl, 4-methylthienylacetyl, 3-isothiazolylacetyl, 4-methoxyisothiazolylacetyl, 4-isothiazolylacetyl, 3-methylisothiazolylacetyl, 5-isothiazolylacetyl, 3-chloroisothiazolylacetyl, 3-methyl-1,2,5-oxadiazolylacetyl, 1,2,5-thiadiazolyl-4-acetyl, 3-methyl-1,2,5-thiadiazolyl-4-acetyl, 3-chloro-1,2,5-thiadiazolyl-4-acetyl, 3-methoxy-1,2,5-thiadiazolyl-4-acetyl, phenylthioacetyl, 4-pyridylthioacetyl, cyanoacetyl, tetrazolylacetyl, α-fluorophenylacetyl, D-phenylglycyl, 3-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-sulfaminophenylacetyl, α-hydroxyphenylacetyl, α-tetrazolylphenylacetyl and α-sulfophenylacetyl.

The substituent A can be hydrogen, hydroxy, halo, mercapto, acyloxy, acylthio, substituted hydroxy, substituted mercapto, a quaternary ammonium group, azido, amino or a N-substituted amino group. Alternatively, $CH_2A$ can be replaced by a formyl group.

Thus, $CH_2A$ can be a halomethyl such as chloromethyl, bromomethyl or fluoromethyl.

When A is a substituted hydroxy or substituted mercapto group, the —CH₂A group can be shown by the formula

where Z is oxygen or sulfur, and R₅ is an acyl group; a straight chain or branched chain loweralkyl, alkenyl or alkynyl group; an aryl group; an aralkyl group; or a heterocyclic group such as heteroaryl or heteroalkyl. These groups can be unsubstituted or can be substituted by radicals such as alkyl, alkoxy, halo, cyano, carboxy, carbamoyl, azido, sulfo, amino, substituted amino, haloalkyl, carboxyalkyl, carbamoylalkyl,, N-substituted carbamoylalkyl, guanidino, N-substituted guanidino, guanidinoalkyl, sulfamyl, substituted sulfamyl, and the like. Representative of the groups —CH₂ZR₅ thus represented that might be mentioned are methoxymethyl, n-propoxymethyl, methylthiomethyl, acetoxymethyl, propionyloxymethyl, benzoyloxymethyl, (p-chlorobenzoyl)oxymethyl, (p-methylbenzoyl)oxymethyl, pivaloyloxymethyl, (1-adamantyl)carboxymethyl, butanoyloxymethyl, carbamoyloxymethyl, (N-methylcarbamoyl)oxymethyl, (N-ethylcarbamoyl)oxymethyl, [N-(2-chloroethyl)carbamoyl]oxymethyl, (N-phenylcarbamoyl)oxymethyl, (N-p-sulfophenylcarbamoyl)oxymethyl, p-carboxymethylphenylcarbamoyloxymethyl, methoxycarbonyloxymethyl, isobutanoyloxymethyl, cyclobutylcarbonyloxymethyl, carbamoylthiomethyl, (ethoxythiocarbonyl)thiomethyl, (n-propoxythiocarbonyl)thiomethyl, (cyclopentanoxythiocarbonyl)-thiomethyl, methylthiomethyl, N,N-diethylthiocarbamoylthiomethyl, N-methylpiperazinium-1-thiocarbonylthiomethyl, N,N-dimethylpiperazinium-1-thiocarbonylthiomethyl, 2-furoylthiomethyl, isothiouroniummethyl, (5-methyl-1,3,4-thiadiazol-2yl)thiomethyl, p-tolylsulfonylthiomethyl, mesyloxymethyl, 1-methyl-1,2,3,4-tetrazolyl-5-thiomethyl, tosyloxymethyl, sulfamoyloxymethyl, 1-naphthoyloxymethyl, 2-furylacetoxymethyl, cinnamoyloxymethyl, p-hydroxycinnamoyloxymethyl, p-sulfocinnamoyloxymethyl and 1R:2S-epoxypropylphosphonyloxymethyl, benzyloxymethyl, p-methoxybenzyloxymethyl, p-nitrobenzyloxymethyl, (N-2,2,2-trichloroethyl)carbamoyloxymethyl, N,N-bis(p-methoxybenzyl)carbamoyloxymethyl.

Alternatively, when CH₂A is hydroxymethyl, the cephalosporin can also exist as the lactone which is formed by internal esterification with the carboxy group.

The substituent CH₂A can also be a group of the general formula

wherein Y₁ represents amino or substituted amino including nitrogen heterocycles and substituted heterocyclic groups. Examples of such groups that might be mentioned are aminomethyl, acetamidomethyl, carbamoylaminomethyl, N,N-dimethylaminomethyl, N-(2-chloroethyl)aminomethyl, 5-cyano-triazol-1-ylmethyl, 4-methoxycarbonyltriazol-1-ylmethyl.

When A is amino the cephalosporin compound can also exist as the lactam formed by loss of water with the adjacent carboxy group.

Representative of the quaternary ammonium groups representing A that might be mentioned are pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-N-carbomethoxy carbamoyl)pyridinium, 4-(N-cyanocarbamoyl)pyridinium, 4-(carboxymethyl)pyridinium, 4-(hydroxymethyl)pyridinium, 4-(trifluoromethyl)pyridinium, quinolinium, picolinium and lutidinium.

The preferred groups representing A are hydrogen, carbamoyloxy, mono and di-substituted carbamoyloxy wherein the substituents are lower alkyl of 1–6 carbon atoms (e.g. methyl, ethyl, propyl, butyl, pentyl etc.) halo, azido, cyano, hydroxy, alkoxy, aryloxy, aralkyloxy, heterocycleoxy, mercapto, alkylthio, arylthio, aralkylthio, heterocyclethio, amino, alkylamino, alkanoylamino, hydroxyphenyl, acylthio, acyloxy, isothiouronium, sulfamoyloxy, quaternary ammonium, a heterocyclic tertiary amine, alkylsulfonyloxy and (cis-1,2-epoxypropyl)phosphono. The heterocycles can be a 5 or 6-membered hetero ring containing one or more nitrogen, oxygen or sulfur atoms. The acyl group can be a loweralkanoyl group of 2–6 carbon atoms, carbamoyl, or thiocarbamoyl and N-alkyl or N,N-dialkyl derivatives thereof. The alkyl group of the foregoing substituents contains 1–6 carbon atoms and may be further substituted radicals such as alkoxy, halo, amino, cyano, carboxy, sulfo, and the like.

The carboxyl blocking group (R₆) is, preferably, an ester formed with an alcohol or phenol which may readily be split off at a later stage of the reaction.

Generally, it is preferred to carry out the reaction with a compound wherein the carboxy group is blocked or protected since maximum yields of the desired product are obtained with such derivatives. It is preferable that a protecting group be utilized which can be removed to obtain the free acid without disruption of the β-lactam moiety.

The group protecting the carboxyl group may be formed with an alcohol (aliphatic or araliphatic), phenol, silanol, stannanol or acid which may readily be split off at a later stage of the reaction.

Suitable esters thus include compounds containing as the 4-ester group, a group selected from the following list which is representative and not intended to be an exhaustive list of possible ester groups:

(i) — COOCR$^a$R$^b$R$^c$ wherein at least one of R$^a$, R$^b$ and R$_c$ is an electron-donor, e.g. p-methoxyphenyl, 2,4,6-trimethylphenyl, 9-anthryl, methoxy, CH₂SCH₃, tetrahydrofur-2-yl, tetrahydropyran-2-yl or fur-2-yl. The remaining R$^a$, R$^b$ and R$^c$ groups may be hydrogen or organic substituting groups. Suitable ester groups of this type include p-methoxybenzyloxycarbonyl and 2,4,6-trimethylbenzyloxycarbonyl.

(ii) — COOCR$^a$R$^b$R$^c$ wherein at least one of R$^a$, R$^b$ and R$^c$ is an electron-attracting group, e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining R$^a$, R$^b$ and R$^c$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) — COOCR$^a$R$^b$R$^c$ wherein at least two of R$^a$, R$^b$ and R$^c$ are hydrocarbon such as alkyl e.g. methyl or ethyl, or aryl e.g. phenyl and the remaining R$^a$, R$^b$ and R$^c$ group, if there is one, is hydrogen. Suitable esters of this type include t-butyloxycarbonyl, t-amyloxycarbonyl, diphenylmethoxycarbonyl and triphenylmethoxycarbonyl.

(iv) —COOR$^d$ wherein R$^d$ is adamantyl, 2-benzyloxyphenyl, 4-methylthiophenyl or tetrahydropyran-2-yl.

Silyl esters may conveniently be prepared from a halosilane or a silazane of the formula R$^4$$_3$SiX; R$^4$$_2$SiX$_2$; R$^4$$_3$Si.NR$^4$$_2$; R$^4$$_3$SiR$^4$$_3$; R$^4$$_3$Si.NH.COR$^4$; R$^4$$_3$Si.NH.CO.NH.SiR$^4$$_3$; R$^4$NH.CO.NR$^4$.SiR$^4$$_3$; or R$^4$C(OSiR$^4$$_3$):NSiR$^4$$_3$ where X is a halogen and the various groups R$^4$, which can be the same or different,, represent hydrogen atoms or alkyl, e.g. methyl, ethyl, n-propyl, iso-propyl; aryl, e.g. phenyl; or aralkyl, e.g. benzyl groups.

Preferred derivatives of silanols are silyl chlorides such as for example trimethylchlorosilane and dimethyldichlorosilane.

Protecting groups of particular interest include alcohols and phenols, and the like. R$_6$ is preferably an alkyl or aralkyl group containing from 1 to about 20 carbon atoms. Thus, R$_6$ can be a lower alkyl group such as methyl, ethyl or tertiary butyl, a substituted alkyl such as phthalimidomethyl, succinimidomethyl, phenacyl, substituted phenacyl such as p-bromophenacyl, a β-substituted ethyl group such as 2,2,2-trichloroethyl, 2-methylthioethyl or 2-(p-methylphenyl)ethyl, an alkoxyalkyl group such as methoxymethyl, an aryloxyalkyl such as p-methoxyphenoxymethyl, an aralkyloxyalkyl group such as benzyloxymethyl, a substituted benzyl group such as p-nitrobenzyl, p-methoxybenzyl, 3,5-dinitrobenzyl, 2,4,6-trimethylbenzyl or 3,5-dichloro-4-hydroxybenzyl, benzhydryl or a substituted benzhydryl group such as p-methoxybenzhydryl, and the like. Preferred blocking groups are methyl, tertiary butyl, phenacyl, p-bromophenacyl, 2,2,2-trichloroethyl, p-methoxybenzyl, benzhydryl, p-nitrobenzyl, methoxymethyl and p-methoxyphenoxymethyl.

The term "blocking group" as utilized herein is employed in the same manner and in accordance with the teaching of U.S. Pat. No. 3,697,515; the contents therein with respect to said blocking group being incorporated herein by reference.

The carboxyl groups may be regenerated from an ester by any of the usual methods; for example, acid- and base-catalysed hydrolysis (especially for silyl and stannyl esters) is generally applicable, as well as enzymically-catalysed hydrolyses; however, aqueous mixtures may be poor solvents for these compounds and they may cause isomerizations, rearrangements, side-reactions, and general destruction, so that special methods may be desirable. Five suitable methods of deesterification are:

A— Reactions with Lewis acids: Suitable Lewis acids for reaction with the esters include trifluoroacetic acid, formic acid, hydrochloric acid in acetic acid, zinc bromide in benzene and aqueous solutions or suspensions of mercuric compounds. The reaction with the Lewis acid may be improved by addition of a nucleophile such as anisole.

B— Reduction: Suitable systems for effecting reduction are zinc/acetic acid, zinc/formic acid, zinc/lower alcohol, zinc/pyridine, palladised-charcoal and hydrogen, electrolysis, and sodium and liquid ammonia.

C— Attack by nucleophiles: Suitable nucleophiles are those containing a nucleophilic oxygen or sulphur atom for example alcohols, mercaptans and water.

D— Oxidative methods: For example, which involve the use of hydrogen peroxide and acetic acid.

E— Irradiation.

Of particular interest are the procedures involving cleavage of groups such as benzhydryl, tertiary butyl, p-bromophenacyl, p-methoxybenzyl, p-methoxyphenoxymethyl and methoxymethyl with an acid such as trifluoroacetic acid and cleavage of the 2,2,2-trichloroethyl and phenacyl groups by reaction with zinc and acetic acid.

It may be noted that in the process described above, the substituent at the 3-position of the cephalosporin nucleus may be converted to or readily replaced by other A substituents pursuant to methods well known in this art. For example, upon treating the 3-acetoxymethyl substituted cephalosporanates with a suitable reagent or combination of reagents, it is possible to substitute various substituents for acetoxy at the 3-position of the cephalosporin nucleus. Suitable reagents include, for example, alkali metal toluenesulfinates, alkali metal azide, polyhydroxybenzene, N-loweralkyl indole, thiourea, mercaptans, phosphorus pentachloride, thiocyanates, cycloalkyl xanthates, pyridine, thiobenzoic acid, N-alkyl and N,N-dialkylthioureas, or alkali metal N-alkyl and N,N-dialkylthiocarbamates and the like.

Thus by reaction with a heterocyclic thiol, for example, 1-methyl-1,2,3,4-tetrazole-5-thiol or 5-methyl-1,3,4-thiadiazole-2-thiol the 3-acetoxy cephalosporin is converted to the corresponding heterothiomethyl compound.

Thus, by reaction with a quaternary ammonium compound, for example pyridine, the 3-acetoxy cephalosporin is converted to the corresponding 3-pyridinomethyl compound. Alternatively, the 3-acetoxy cephalosporins upon treatment with citrus acetylesterase are converted to the corresponding 3-hydroxymethyl compounds which can be acylated to produce other 3-acyloxymethyl including carbamoyloxymethyl, or acylthiomethyl compounds. Similarly, other 3-substituted cephalosporin compounds are prepared following procedures well known in this art.

One method for the introduction of an N,N-diloweralkylcarbamoyloxymethyl or heterocyclic aminocarbonyloxymethyl moiety at position 3 of the instant products consists in treating a 3-hydroxymethyl analog such as 3-hydroxymethyl-7-methoxy-7-(2-thienylacetamido)cephalosporanic acid with phosgene and a diloweralkylamine in the presence of a base. In this manner the following products can be obtained: sodium dl-3-(N,N-dimethylcarbamoyloxymethyl)-7-methoxy-7-(2-thienylacetamido)decephalosporanate and sodium dl-3-(pyrrolidinylcarbonyloxymethyl)-7-methoxy-7-(2-thienylacetamido)decephalosporanate.

The N-mono substituted carbamoyloxymethylcephalosporin products may be obtained by treating a 3-hydroxymethyl-7-amidodecephalosporanate with a suitable isocyanate. In this manner sodium dl-3-(N-methylcarbamoyloxymethyl)-7-methoxy-7-(2-thienylacetamido)decephalosporanate is obtained by treating sodium dl-3-hydroxymethyl-7-methoxy-7-(2-thienylacetamido)decephalosporanate with methylisocyanate in the presence of sodium bicarbonate.

The unsubstituted carbamoyloxymethyl may be obtained by cleaving an N-mono- or di-substituted carbamoyloxymethyl material such as N,N-di-p-methoxybenzylcarbamoyloxymethyl or N-2,2,2-trichloroethyl carbamoyloxymethyl. An alternative method for obtaining the carbamoyloxymethyl group at the 3-position involves treating the 3-hydroxymethyl analog with trichloroacetylisocyanate or chlorosulfonylisocyanate, followed by hydrolysis.

The acylated glycine starting materials (I) are known materials and may be prepared using techniques well known to the art. For example, glycine may be conveniently reacted with an acyl halide in the presence of a base such as sodium bicarbonate to produce the N-(acyl)glycine. Conversion of the free carboxy group of the glycine to the desired anhydride, acid halide, ester or trifluoromethanesulfonate may be accomplished using well known procedures. For example, the N-acylated glycine may be converted to a mixed anhydride using a reagent such as isobutylchloroformate; the acid halide produced via treatment with reagents such as $PCl_5$. The ester is prepared by treatment with an appropriate alcohol and the trifluoromethanesulfonate derivative effected by reacting the acylated glycine chloride with silver trifluoromethanesulfonate.

The thiazine reactant (II) may be prepared in accordance with the procedures set forth in copending application Ser. No. 336,561, filed Mar. 5, 1973 in the names of Burton G. Christensen and Ronald W. Ratcliffe, said procedures incorporated herein by reference.

The thiazines may be prepared as follows:

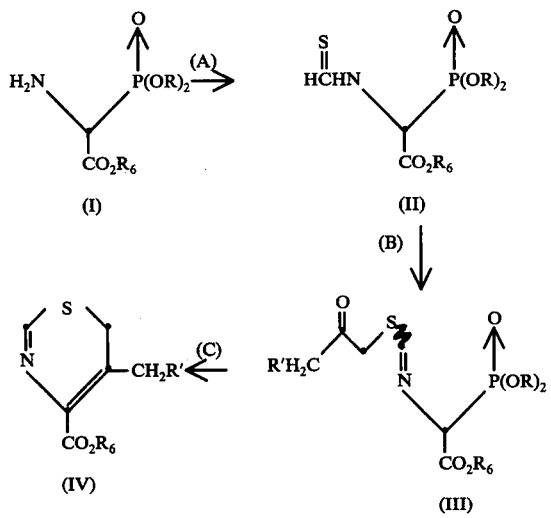

In process (A) the starting material, an ester of α-aminophosphonoacetic acid (I) is reacted with a thionoformate ester to produce the corresponding thioformamido ester (II). Various esters of the starting material (I) can be utilized in the above process. Thus, phosphono esters, as for example the diloweralkyl esters, or the diaryl esters, are suitable for use in this process.

Representative of the esters that may be employed include those wherein R may be the same or different, and is, for example, methyl, ethyl, propyl, butyl, pentyl, phenyl, benzyl and the like. The carboxy group of the phosphono starting material may be blocked or protected, preferably by the use of a group $R_6$, previously defined which can be ultimately removed to obtain the free acid form of the cephalosporin without disruption of the β-lactam moiety. As indicated previously, protecting groups suitable for this purpose are indeed well known in this art.

Examples of representative starting materials (I) that might be mentioned are trichloroethyl α-amino-diethylphosphonoacetate, trichloroethyl α-amino-diphenylphosphonoacetate, phenyl α-amino-dimethylphosphonoacetate, p-methoxybenzyl α-amino-diethylphosphonoacetate, benzhydryl α-amino-diphenylphosphonoacetate, t-butyl α-amino-dimethylphosphonoacetate, t-butyl α-amino-dipropylphosphonoacetate, methyl α-amino-diphenylphosphonoacetate, phenacyl or p-bromophenacyl α-amino-diethylphosphonoacetate, methoxymethyl α-amino-dimethylphosphonoacetate, p-methoxyphenoxymethyl α-amino-dimethylphosphonoacetate, and p-nitrobenzyl α-aminodimethylphosphonoacetate.

Process (A) involving the conversion of compound (I) to the corresponding thioformamido derivative (II) is carried out by reacting the phosphonoacetate with an ester of thionoformic acid such as a lower alkyl ($C_1$–$C_6$) ester at a temperature varying from 0° C. to 100° C. For example, the reaction may be carried out with ethyl thionoformate at 0° C. Generally, it is preferred to carry out the reaction in an inert solvent media such as benzene, carbon tetrachloride, methylene chloride or hexane. Alternatively, the reaction is carried out in the presence of liquid hydrogen sulfide at room temperature. After completion of the reaction, the solvent is evaporated to afford the desired product.

Alternative processes of thioformylating the α-aminophosphonoacetate include the following:

(a) O-Ethyl thioformate or ethyl thionoformate at 0° C. to 30° C. in solvents such as $CCl_4$, $CH_2Cl_2$, $H_2S$ or in the absence of a solvent;

(b) Sodium dithioformate or potassium dithioformate at 0° C. to 30° C in solvents such as $H_2O$, $H_2O$-ether $H_2O$—EtOH or $H_2O$—MeOH;

(c) $H_2S$ + HCN at 0° to 30° C. in solvents such as MeOH, EtOH, $H_2O$, $H_2O$—MeOH or $H_2O$—EtOH.

Step (B) of the process comprises reacting the thioformamido intermediate (II) with a substituted acetone of the general formula $R'CH_2COCH_2X$ wherein R' represents hydrogen; lower alkoxy such as methoxy, propoxy, etc., aryloxy (phenoxy, etc.), aralkyloxy (benzyloxy, etc.), a lower alkoxy lower alkoxy group such as methoxymethoxy or a heterocyclic thio group such as 5-(1-methyltetrazolyl)thio and 2-(5-methyl-1,3,4-thiadiazolyl)thio; halo (chloro, bromo, fluoro); an acyloxy group such as acetoxy, isobutryloxy and the like; carbamoyloxy; N-substituted carbamoyloxy; N,N-disubstituted carbamoyloxy wherein the substituents may be alkyl (preferably lower alkyl of 1–6 carbon atoms; e.g., methyl, ethyl, propyl, t-butyl, hexyl); halogenated lower alkyl (e.g., trichloroethyl, etc.); lower alkoxy of 1–6 carbon atoms, benzyl, substituted benzyl such as p-methoxybenzyl, p-methoxyphenethyl, phenethyl and substituted phenethyl such as p-methoxyphenethyl, p-aminophenethyl, etc.) or halo (chloro, bromo, fluoro). The term lower alkyl as used herein refers to alkyl groups having 1–6 carbon atoms. X is halogen (bromo, fluoro, iodo or chloro), mesyloxy, tosyloxy, or trifluoromethylsulfonyloxy. The reaction may be carried out at temperatures varying from 0° C. to 50° C. in the presence of an acid scavenger to produce the corresponding S-substituted thioformimidate compound (III). Thus, the reaction is conveniently carried out by reacting the intermediate product II with the halo-substituted acetone in the presence of about one equivalent of an inorganic base such as an alkali metal carbonate, for example, NaH, potassium carbonate or non-nucleophilic organic bases such as diazobicyclononane and bis-1,8-(dimethylamino)naphthalene, at room temperature. After the reaction is complete, the product is conveniently isolated by filtering the reaction mixture and evaporating the filtrate to dryness.

Representative examples of the substituted acetones that may be employed are chloro-acetone, 1-chloro-3-acetoxyacetone, 1-chloro-3-(N-trichloroethylcarbamoyloxy)acetone, 1-chloro-3-methoxymethoxy-propan-2-one, 1-chloro-3-phenoxyacetone, 1-chloro-3-(p-methoxybenzyloxy)acetone, 1-chloro-3-isobutyryloxy-2-propanone, 1-chloro-3-benzyloxyacetone, 1-chloro-3-(p-nitrobenzyloxy)acetone, 1-bromo-3-methoxymethoxyacetone and 1-chloro-3-methoxyacetone. The substituted acetone compounds are known compounds or can be readily prepared pursuant to methods known in the art. For example, the 1-chloro-3-carbamoyloxyacetone is prepared by converting 1-chloro-3-acetoxyacetone to the dimethylketal, hydrolyzing this product to the 3-hydroxy compound, and reacting this product with sodium cyanate and trifluoroacetic acid in methylene chloride. An alternative method for the preparation of the substituted acetone involves conversion of the acid to the acid halide; reaction of the acid halide to produce the corresponding diazomethyl ketone which is then treated with HCl to produce the chloromethyl ketone as follows:

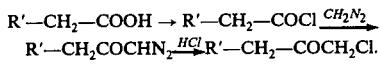

R'—CH₂—COOH → R'—CH₂—COCl $\xrightarrow{CH_2N_2}$
R'—CH₂COCHN₂ $\xrightarrow{HCl}$ R'—CH₂—COCH₂Cl.

The intermediate S-substituted thioformimidate compound (III) upon reaction with a base such as an alkali metal carbonate or hydride or an organo lithium compound such as phenyllithium is converted to the corresponding thiazine compound (IV) [Step C]. Alternatively, the thiazine may be produced by the condensation of the thioformamido derivative (II) and the substituted acetone in the presence of more than about one equivalent of the base. Thus, the thiazine is produced almost exclusively when two or more equivalents of potassium carbonate are used in the condensation reaction.

Examples of representative thiazine compounds (IV) that might be mentioned are p-methoxybenzyl 5-acetoxymethyl-6H-1,3-thiazine-4-carboxylate, methyl 5-methyl-6H-1,3-thiazine-4-carboxylate, 2,2,2-trichloroethyl 5-benzyloxy methyl-6H-1,3-thiazine-4-carboxylate, p-methoxybenzyl 5-carbamoyloxymethyl-6H-1,3-thiazine-4-carboxylate, methoxymethyl 5-isobutryloxymethyl-6H-1,3-thiazine-4-carboxylate, p-methoxybenzyl-5-(N,N-di-p-methoxybenzyl)-carbamoyloxymethyl-6H-1,3-thiazine-4-carboxylate, p-methoxybenzyl 5-(N-2,2,2-trichloroethyl)-carbamoyloxymethyl-6H-1,3-thiazine-4-carboxylate and the like. The α-aminophosphonoacetate ester (I) used as the starting material in the process described above is obtained by the processes shown in the following flowsheet:

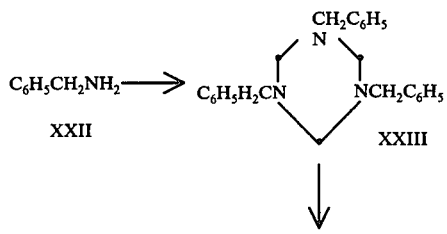

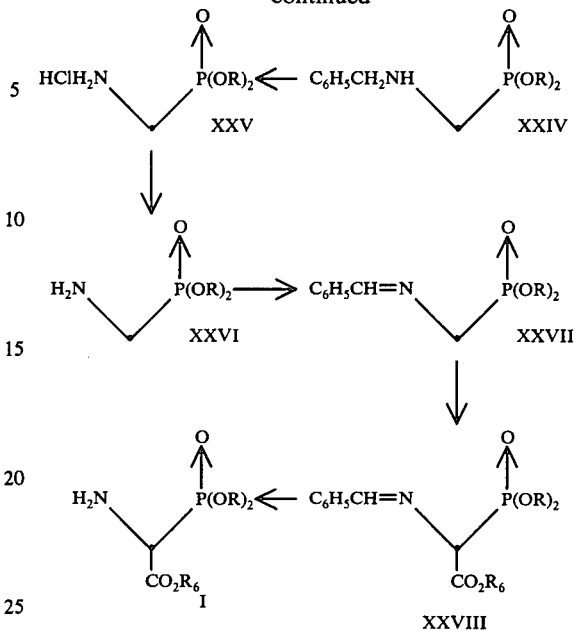

wherein R and R₆ are as defined above.

In accordance with the above-depicted reactions, benzylamine is first reacted with formaldehyde to obtain the 1,3,5-tribenzyl-sym-hexahydrotriazine XXIII. The latter compound on reaction with a di-substituted phosphite is converted to the phosphonate XXIV. This reaction is conveniently effected by heating a mixture of the disubstituted phosphite with the triazine at 100° C. for sufficient time to complete the formation of the desired intermediate product which is conveniently isolated as an acid salt, such as the hydrochloride. Reduction of the intermediate N-benzylaminomethylphosphonate acid salt in the presence of palladium on carbon affords the salt of the corresponding amino compound XXV. The acid salt is converted to the amine by reacting it with ammonia in a suitable solvent medium such as chloroform. After removing the precipitated ammonium salt, the desired product is readily recovered by evaporating the solvent to obtain the aminomethylphosphonate ester XXVI. Alternatively, the acid salt XXV is neutralized with aqueous K₂HPO₄ and the free amine XXVI is extracted into an organic solvent such as CH₂Cl₂. This latter product on reaction with an aldehyde such as benzaldehyde is converted to the corresponding Schiff base XXVII, which on reaction with a strong base e.g. an organolithium compound such as phenyllithium and then a haloformate ester is converted to the imine XXVIII. Treatment of this imine with 2,4-dinitrophenyl hydrazine in the presence of p-toluenesulfonic acid monohydrate or with p-toluenesulfonic acid hydrate in ether followed by neutralization of the amine acid salt affords the desired α-aminophosphonoacetate ester (I).

In carrying out the reactions described herein it is preferred to protect groups such as carboxy groups, mercapto groups, amino groups or hydroxy groups. Maximum yields are obtained by employing these protected compounds. Examples of carboxy protecting groups are trichloroethyl, tert-butyl, benzoylmethyl, p-methoxybenzyl, benzyl, benzhydryl, trityl, trimethylsilyl, methoxymethyl, tert-butyloxycarbonyl and the like. These ester groups may be removed by methods well known to those skilled in the art; for example, the benzhydryl or p-nitrobenzyl groups may be removed by hydrogenation in the presence of a catalyst such as palladium-on-carbon or by treatment with a strong organic or inorganic acid. The tert-butyl or methoxymethyl groups may also be removed by treatment with strong organic or inorganic acid. Examples of these acids are hydrochloric acid, sulfuric acid, boron trifluoride etherate, formic acid, trifluoroacetic acid, trichloroacetic acid, nitrobenzoic acid and the like.

Amino protecting groups are well known in the art and are described, for example, in U.S. Pat. Nos. 2,479,295 through 2,479,297; 2,562,407 through 2,562,411 and 2,623,876. Groups such as triphenylmethyl and trimethylsilyl may be employed. The groups set forth in the indicated patents are incorporated herein by reference. In addition, protective groups formed by reagents such as 1-fluoro-2,4-dinitrobenzene, 1-fluoro-2-nitro-4-carbomethoxy-benzene, p-toluenesulfonyl chloride, phenylisocyanate and methylchloroformate may be employed in the practice of the invention.

Typical of hydroxy or mercapto protecting groups which may be utilized include tetrahydropyranyl ether, benzyl, ether, p-nitrobenzyl ether or p-methoxybenzyl ether. These groups may be subsequently converted to the free hydroxy group by mild aqueous hydrolysis or by hydrogenation.

EXAMPLE 1

N-(2-thienylacetyl) glycine

One gram of glycine is stirred in 20 ml water-acetone 1:1 with two equivalents sodium bicarbonate at 25°, and one equivalent of 2-thienylacetyl chloride in 5 ml acetone is added over one-half hour. After another fifteen minutes of stirring the solution is diluted with water and the N-(2-thienylacetyl) glycine filtered and dried.

When other representative acyl halides are used in place of 2-thienylacetyl chloride in the above process, the corresponding acyl glycine is obtained. For example, when the following acyl halides are employed: phenacetyl chloride, 3-bromophenylacetyl chloride, p-protectedamino methylphenylacetyl chloride, 4-protectedcarboxylmethylphenylacetyl chloride, 4-carboxamidomethylphenylacetyl chloride, 2-furylacetyl chloride, 5-nitrofurylacetyl chloride, 3-furylacetyl chloride, 2-thienylacetyl chloride, 5-chlorothienylacetyl chloride, 5-methoxythienylacetyl chloride, α-guanidino-2-thienylacetyl chloride, 3-thienylacetyl chloride, 4-methylthienylacetyl chloride, 3-isothiazolylacetyl chloride, 4-methoxyisothiazolylacetyl chloride, 4-isothiazolylacetyl chloride, 3-methylisothiazolylacetyl chloride, 5-isothiazolylacetyl chloride, 3-chloroisothiazolylacetyl chloride, 3-methyl-1,2,5-oxadiazolylacetyl chloride, 1,2,5-thiadiazolyl4-acetyl chloride, 3-methyl-1,2,5-thiadiazolyl-4-acetyl chloride, 3-chloro-1,2,5-thiadiazolyl-4-acetyl chloride, 3-methoxy-1,2,5-thiadiazolyl-4-acetyl chloride, phenylthioacetyl chloride, 4-pyridylthioacetyl chloride, cyanoacetyl chloride, tetrazolylacetyl chloride, α-fluorophenylacetyl chloride, D-protectedphenylglycyl chloride, 3-protectedhydroxy-D-phenylglycyl chloride, 2-thienylglycyl chloride, 3-thienylmalonyl chloride, α-protectedphosphonophenylacetyl chloride, α-sulfaminophenylacetyl chloride, α-protectedhydroxyphenylacetyl chloride, α-tetrazolylphenylacetyl chloride and α-sulfophenylacetyl chloride.

The following acyl glycines are obtained: N-(phenacetyl)glycine, N-(3-bromophenylacetyl)glycine, N-(p-aminomethylphenylacetyl)glycine, N-(4-carboxylmethylphenylacetyl)glycine, N-(4-carboxamidomethylphenylacetyl)glycine, N-(2-furylacetyl)glycine, N-(5-nitrofurylacetyl)glycine, N-(3-furylacetyl)glycine, N-(2-thienylacetyl)glycine, N-(5-chlorothienylacetyl)glycine, N-(5-methoxythienylacetyl)glycine, N-(α-guanidino-2-thienylacetyl)glycine, N-(3-thienylacetyl)glycine, N-(4-methylthienylacetyl)glycine, N-(3-isothiazolylacetyl)glycine, N-(4-methoxyisothiazolylacetyl)glycine, N-(4-isothiazolylacetyl)glycine, N-(3-methylisothiazolylacetyl)glycine, N-(5-isothiazolylacetyl)glycine, N-(3-chloroisothiazolylacetyl)glycine, N-(3-methyl-1,2,5-oxadiazolylacetyl)glycine, N-(1,2,5-thiadiazolyl-4-acetyl)glycine, N-(3-chloro-1,2,5-thiadiazolyl-4-acetyl)glycine, N-(phenylthioacetyl)glycine, N-(4-pyridylthioacetyl)glycine, N-(cyanoacetyl)glycine, N-(tetrazolylacetyl)glycine, N-(α-fluorophenylacetyl)glycine, N-(D-phenylglycyl)glycine, N-(3-hydroxy-D-phenylglycyl)glycine, N-(2-thienylglycyl)glycine, N-(3-thienylglycyl)glycine, N-(phenylmalonyl)glycine, N-(3-chlorophenylmalonyl)glycine, N-(2-thienylmalonyl)glycine, N-(3-thienylmalonyl)glycine, N-(α-phosphonophenylacetyl)glycine, N-(α-sulfaminophenylacetyl)glycine, N-(α-hydroxyphenylacetyl)glycine, N-(α-tetrazolylphenylacetyl)glycine, and N-(α-sulfophenylacetyl)glycine.

EXAMPLE 2 p-Methoxybenzyl 7-(2-thienylacetamido)cephalosporanate

One millimole of N-(2-thienylacetyl)glycine in 10 ml methylene chloride at 0° is treated successively with one millimole each of triethylamine and isobutyl chloroformate, forming N-(2-thienylacetyl)glycylisobutyl carbonate. To this solution at −78° is added one equivalent of p-methoxybenzyl. 5-acetoxymethyl 6H-1,3-thiazine-4-carboxylate and then a second millimole of triethylamine. The reaction mixture is allowed to warm to room temperature over one hour, and kept at 25° one hour. The mixture is then washed successively with aqueous pH 2 buffer, water, and aqueous bicarbonate, dried with MgSO$_4$, filtered and evaporated, affording p-methoxybenzyl 7-(2-thienylacetamido) cephalosporanate which may be purified if desired by chromatography on silica gel, eluting with 4:1 chloroform-ethyl acetate.

When other representative thiazines are used in place of methoxybenzyl 5-acetoxymethyl 6H-1,3-thiazine 4-carboxylate in the above process the corresponding cephalosporin is obtained. For example, when the following thiazines are employed: methyl 5-methyl-6H-1,3-thiazine-4-carboxylate, 2,2,2-trichloroethyl 5-benzyloxymethyl-6H-1,3-thiazine-4-carboxylate, p-methoxybenzyl 5-carbamoyloxymethyl-6H-1,3-thiazine-4-carboxylate, methoxymethyl 5-isobutryloxymethyl-6H-1,3-thiazine-4-carboxylate, p-methoxybenzyl-5-(N,N-di-p-methoxybenzyl)-carbamoyloxymethyl-6H-1,3-thiazine-4-carboxylate and p-methoxybenzyl 5-(N-2,2,2-trichloroethyl)-carbamoyloxymethyl-6H-1,3-thiazine-4-carboxylate.

The following cephalosporins are obtained: methyl 7-(2-thienylacetamido)-3-methyl decephalosporanate;

2,2,2-trichloroethyl 7-(2-thienylacetamido)-3-benzyloxymethyl-3-cephem-4-carboxylate; p-methoxybenzyl-7-(2-thienylacetamido)-3-carbamoyloxymehtyl-3-cephem-4-carboxylate; methoxymethyl-7-(2-thienylacetamido)-3-isobutryloxymethyl-3-cephem-4-carboxylate; p-methoxybenzyl 7-(2-thienylacetamido)-3-N,N-di-p-methoxybenzyl)-carbamoyloxymethyl-3-cephem-4-carboxylate and p-methoxybenzyl 7-(2-thienylacetamido)-3-(N-2,2,2-trichloroethyl)carbamoyloxymethyl-3-cephem-4-carboxylate.

EXAMPLE 3

P-Methoxybenzyl-7-phenylacetamido-3-methyl decephalosporanate

One millimole P-methoxybenzyl-5-methyl-6H-1,3-thiazine-4-carboxylate in 10 ml methylene chloride at −78° is treated with one millimole each of triethylamine and 2-benzylidene-4,5-diketo-3-oxazolidinacetyl chloride. The reaction mixture is allowed to warm up to room temperature over one hour, and kept at 25° one hour, affording crude p-methoxybenzyl 7-(3-oxazolidinyl)-3-methyl decephalosporanate.

The solvent is evaporated and replaced with 15 ml dioxane. Benzylamine, 2.2 millimoles, is added, and the mixture kept overnight at 25°, and then 2 hours at 65°. The dioxane is pumped off in vacuo and replaced with benzene. The solution is washed successively with pH 2 buffer, water, and aqueous bicarbonate, dried with MgSO$_4$, filtered, and evaporated. The crude p-methoxybenzyl-7-phenylacetamido-3-methyl decephalosporanate thus obtained is purified by chromatography on silica gel, eluting with 4:1 chloroformethyl acetate.

EXAMPLE 4 p-Bromphenacyl 7-t-butoxycarbonylamino-3-isobutyroyloxymethyl decephalosporanate One millimole of t-butoxycarbonyl glycine in 10 ml methylene chloride at 0° is treated successively with one millimole each of triethylamine and ethyl chloroformate. To this solution at −78° is added one millimole of p-bromophenacyl 5-isobutyroyloxymethyl-6H-1,3 thiazine-4-carboxylate and then a second millimole of triethylamine. The reaction mixture is allowed to warm to room temperature over one hour, and kept at 25° one hour. The mixture is then washed successively with aqueous pH 2 buffer, water, and aqueous bicarbonate, dried with MgSO$_4$, filtered, evaporated, and chromatographed on silica gel, eluting with 4:1 chloroformethyl acetate, affording pure p-bromophenacyl 7-t-butoxycarbonylamino-3-isobutyroyloxymethyl decephalosporanate.

EXAMPLE 5 p-Bromophenacyl 7-amino-3-isobutyroyloxymethyl decephalosporanate p-Bromophenacyl 7-t-butoxycarbonylamino-3-isobutyroyloxymethyl decephalosporanate obtained above is dissolved in 0.2 ml anisole and 1 ml trifluoroacetic acid. After one-half hour at 25°, the mixture is pumped at 0.1 mm at 30°, taken up in water, washed with ether, adjusted to pH 8 and extracted into ethyl acetate. After drying with MgSO$_4$, filtration and evaporation, p-bromophenacyl 7-amino-3-isobutyroyloxymethyl decephalosporanate is obtained.

EXAMPLE 6

2-(2-Thiophenemethylidene)-4,5-diketo-oxazolidinacetic acid

N-2-thienylacetyl glycine, 8 g, and 8 ml oxalyl chloride are stirred 16 hours in 450 ml ether, forming 2-(2-thiophenemethylidene)-4,5-diketo-oxazolidinacetic acid which is filtered and dried.

EXAMPLE 7

2-(2-Thiophenemethylidene)-4,5-diketo-oxazolidinacetyl chloride 2-(2-Thiophenemethylidene)-4,5-diketo-oxazolidinacetic acid, 1g., 20 ml benzene, 5 ml thionyl chloride and 1 drop pyridine are kept for 2 hours at 60°–80°, filtered hot and cooled. The product 2-(2-thiophenemethylidene)-4,5-diketo-oxazolidinacetyl chloride crystallizes out and is isolated by filtration.

EXAMPLE 8 p-Bromophenacyl-7-(2-thienylacetamido)-isobutyroyloxymethyl decephalosporanate

One millimole p-bromophenacyl 5-isobutyroyloxymethyl-6H-1,3 thiazine-4-carboxylate in 10 ml CH$_2$Cl$_2$ at −78° is treated with one millimole each of triethylamine and 2-(2-thiophenemethylidene)-4,5-diketo-oxazolidinacetyl chloride. The reaction mixture is warmed to 25° over one hour, and aged 1 hour at 25°, affording p-bromophenacyl-7-[2-(2-thiophenemethylidene)-4,5-diketo-oxazolidinyl]-isobutyroyloxymethyl decephalosporanate.

The solvent is evaporated and replaced with 15 ml dioxane. Benzylamine, 2.2 millimoles, is added, and the mixture kept overnight at 25° and 2 hours at 65°. The dioxane is pumped off in vacuo and replaced with benzene. The solution is washed successively with pH 2 aqueous buffer, water, and aqueous bicarbonate, dried with MgSO$_4$, filtered and evaporated. The crude p-bromophenacyl-7-(2-thienylacetamido)-isobutyroyloxymethyl decephalosporanate thus obtained is purified by chromatography on silica gel, eluting with 4:1 chloroform-ethyl acetate.

EXAMPLE 9 p-Nitrobenzyl 7-t-butoxycarbonylamino-3-methoxymethyl decephalosporanate

One millimole of t-butoxycarbonyl-glycine in 10 ml methylene chloride at 0° is treated successively with one millimole each of triethylamine and isobutyl chloroformate, forming N-(t-butoxycarbonyl)glycyl i-butyl carbonate. To this solution at −78° is added p-nitrobenzyl 5-methoxymethyl 6H-1,3-thiazine-4-carboxylate and then a second millimole of triethylamine. The reaction mixture is allowed to warm to room temperature over one hour, and kept at 25° one hour. The mixture is then washed successively with aqueous pH 2 buffer, water, and aqueous bicarbonate, dried with MgSO$_4$, filtered and evaporated, affording p-nitrobenzyl 7-t-butoxycarbonylamino-3-methoxymethyl decephalosporanate, which may be purified if desired by chromatography on silica gel, eluting with 4:1 chloroform-ethyl acetate.

EXAMPLE 10 p-Nitrobenzyl 7-amino-3-methoxymethyl decephalosporanate

One hundred milligrams of p-nitrobenzyl 7-t-butoxycarbonylamino-3-methoxymethyl decephalosporanate is dissolved in 0.2 ml anisole, and 1 ml trifluoroacetic acid is added. After one-half hour at 25°, the mixture is pumped at 0.1 mm at 30°, taken up in water, washed once with ether, adjusted to pH 8 and extracted into ethyl acetate. After drying with MgSO$_4$, filtration and evaporation of the solvent, p-nitrobenzyl 7-amino-3-methoxymethyl decephalosporanate is obtained.

EXAMPLE 11

Methyl α-methoxy-N-(2-thienylacetyl)glycinate

One gram of methyl α-methoxy glycinate in 25 ml methylene chloride at 0° is treated with one equivalent of triethylamine and then one equivalent of 2-thienylacetyl chloride. After five minutes, the solution is washed successively with water, pH 2 phosphate buffer, water and aqueous bicarbonate. It is then dried with MgSO$_4$, filtered, and evaporated, leaving methyl α-methoxy-N-(2-thienylacetyl)glycinate.

When other representative acyl halides are used in place of 2-thienylacetyl chloride in the above process, the corresponding α-methoxy acyl glycine is obtained. For example, when the following acyl halides are employed: phenacetyl chloride, 3-bromophenylacetyl chloride, 4-carboxylmethylphenylacetyl chloride, 4-carboxamidomethylphenylacetyl chloride, 2-furylacetyl chloride, 5-nitrofurylacetyl chloride, 3-furylacetyl chloride, 2-thienylacetyl chloride, 5-chlorothienylacetyl chloride, 5-methoxythienylacetyl chloride, α-guanidino-2-thienylacetyl chloride, 3-thienylacetyl chloride, 4-methylthienylacetyl chloride, 3-isothiazolylacetyl chloride, 4-methoxyisothiazolylacetyl chloride, 4-isothiazolylacetyl chloride, 3-methylisothiazolylacetyl chloride, 5-isothiazolylacetyl chloride, 3-chloroisothiazolylacetyl chloride, 3-methyl-1,2,5-oxadiazolylacetyl chloride, 1,2,5-thiadiazolyl-4-acetyl chloride, 3-methyl-1,2,5-thiadiazolyl-4-acetyl chloride, 3-chloro-1,2,5-thiadiazolyl-4-acetyl chloride, 3-methoxy-1,2,5-thiadiazolyl-4-acetyl chloride, phenylthioacetyl chloride, 4-pyridylthioacetyl chloride, cyanoacetyl chloride, tetrazolylacetyl chloride, α-fluorophenylacetyl chloride, D-phenylglycyl chloride, 2-thienylglycyl chloride, 3-thienylglycyl chloride, phenylmalonyl chloride, 3-chlorophenylmalonyl chloride, 2-thienylmalonyl chloride, 3-thienylmalonyl chloride, α-phosphonophenylacetyl chloride, α-sulfaminophenylacetyl chloride, α-tetrazolylphenylacetyl chloride and α-sulfophenylacetyl chloride. The following acyl glycines are obtained: α-methoxy-N-(phenacetyl)glycine, α-methoxy-N-(3-bromophenylacetyl)glycine, α-methoxy-N-(4-carboxylmethylphenylacetyl)glycine, α-methoxy-N-(4-carboxamidomethylphenylacetyl)glycine, α-methoxy-N-(4-carboxamidomethylphenylacetyl)glycine, α-methoxy-N-(2-furylacetyl)glycine, α-methoxy-N-(5-nitrofurylacetyl)glycine, α-methoxy-N-(3-furylacetyl)glycine, α-methoxy-N-(2-thienylacetyl)glycine, α-methoxy-N-(5-chlorothienylacetyl)glycine, α-methoxy-N-(5-methoxythienylacetyl)glycine, α-methoxy-N-(α-guanidino-2-thienylacetyl)glycine, α-methoxy-N-(3-thinylacetyl)glycine, α-methoxy-N-(4-methylthienylacetyl)glycine, α-methoxy-N-(3-isothiazolylacetyl)glycine, α-methoxy-N-(4-methoxyisothiazolylacetyl)glycine, α-methoxy-N-(4-isothiazolylacetyl)glycine, α-methoxy-N-(3-methylisothiazolylacetyl)glycine, α-methoxy-N-(5-isothiazolylacetyl)glycine, α-methoxy-N-(3-chloroisothiazolylacetyl)glycine, α-methoxy-N-(3-methyl-1,2,5-oxadiazolylacetyl)glycine, α-methoxy-N-(1,2,5-thiadiazolyl-4-acetyl)glycine, α-methoxy-N-(3-methyl-1,2,5-thiadiazolyl-4-acetyl)glycine, α-methoxy-N-(phenylthioacetyl)glycine, α-methoxy-N-(4-pyridylthioacetyl)glycine, α-methoxy-N-(cyanoacetyl)glycine, α-methoxy-N-(tetrazolylacetyl)glycine, α-methoxy-N-(α-fluorophenylacetyl)glycine, α-methoxy-N-(D-phenylglycyl)glycine, α-methoxy-N-(2-thienylglycyl)glycine, α-methoxy-N-(3-thienylglycyl)glycine, α-methoxy-N-(phenylmalonyl)glycine, α-methoxy-N-(3-chlorophenylmalonyl)glycine, α-methoxy-N-(2-thienylmalonyl)glycine, α-methoxy-N-(3-thienylmalonyl)glycine α-methoxy-N-(α-phosphonophenylacetyl)glycine, α-methoxy-N-(α-sulfaminophenylacetyl)glycine, α-methoxy-N-(α-tetrazolylphenylacetyl)glycine, and α-methoxy-N-(α-sulfophenylacetyl)glycine.

EXAMPLE 12

α-Methoxy-N-(2-thienylacetyl)glycine

One gram of α-methoxy-N-(2-thienylacetyl)glycinate is dissolved in 10 ml methanol at 0°. Over 20 minutes, a solution of one equivalent of 10% KOH in methanol is added. After 15 minutes at 25° the solvent is evaporated and water is added. Addition of dilute HCl precipitates the title compound, which is extracted into ether and isolated by drying with MgSO$_4$, filtering and evaporating ether.

EXAMPLE 13 p-Methoxybenzyl 7-methoxy-7-(2-thienylacetamido)-3-N,N-di-(p-methoxybenzyl)aminocarbonyloxymethyl decephalosporanate One millimole of α-methoxy-N-(2-thienylacetyl)glycine in 10 ml methylene chloride at 0° is treated successively with one millimole each of triethylamine and isobutyl chloroformate, forming α-methoxy-N-(2-thienylacetyl)glycyl i-butyl carbonate. To this solution at −78° is added p-methoxybenzyl-5-N,N-di(p-methoxybenzyl)aminocarbonyloxymethyl 6H-1,3-thiazine-4-carboxylate, and then a second millimole of triethylamine. The reaction mixture is allowed to warm to room temperature over one hour, and kept at 25° one hour. The mixture is then washed successively with aqueous pH 2 buffer, water, and aqueous bicarbonate, dried with MgSO$_4$, filtered and evaporated, affording p-methoxybenzyl 7-methoxy-7-(2-thienylacetamido)-3-N,N-di(p-methoxybenzyl)aminocarbonyloxymethyl decephalosporanate, which may be purified if desired by chromatography on silica gel, eluting with 4:1 chloroformethyl acetate.

When other representative thiazines are used in place of methoxybenzyl 5-acetoxymethyl 6H-1,3-thiazine 4-carboxylate in the above process the corresponding cephalosporin is obtained. For example, when the following thiazines are employed: methyl 5-methyl-6H-1,3-thiazine-4-carboxylate, 2,2,2-trichloroethyl 5-benzyloxymethyl-6H-1,3-thiazine-4-carboxylate, p-methoxybenzyl 5-carbamoyloxymethyl-6H-1,3-thiazine-4-carboxylate, methoxymethyl 5-isobutryloxymethyl-6H-1,3-thiazine-4-carboxylate, p-methoxybenzyl-5-(N,N-di-p-methoxybenzyl)-carbamoyloxymethyl-6H-1,3-thiazine-4-carboxylate and p-methoxybenzyl 5-(N-2,2,2-trichloroethyl)-carbamoyloxymethyl-6H-1,3-thiazine-4-carboxylate.

The following cephalosporins are obtained: methyl 7-methoxy-7-(2-thienylacetamido)-3-methyl decephalosporanate; 2,2,2-trichloroethyl 7-methoxy-7-(2-thienylacetamido)-3-benzyloxymethyl-3-cephem-4-carboxylate; p-methoxybenzyl 7-methoxy-7-(2-thienylacetamido)-3-carbamoyloxymethyl-3-cephem-4-rcarboxylate; methoxymethyl 7-methoxy-7-(2-thienylacetamido)-3-isobutryloxymethyl-3-cephem-4-carboxylate; p-methoxybenzyl 7-methoxy-7-(2-thienylacetamido)-3-(N,N-di-p-methoxybenzyl)-carbamoyloxymethyl-3-cephem-4-carboxylate and p-methoxybenzyl 7-methoxy-7-(2-thienylacetamido)-3-(N-2,2,2-trichloroethyl)-carbamoyloxymethyl-3-cephem-4-carboxylate.

EXAMPLE 14

2,2,2-Trichloroethyl d,l-7β-amino-3-methoxymethyloxymethyl-3-cephem-4-carboxylate and 2,2,2-trichloroethyl d,l-7α-amino-3-methoxymethyloxymethyl-3-cephem-4-carboxylate Step 1. 2,2,2-Trichloroethyl d,l-7β-(p-nitrobenzyloxycarbonylamino)-3-methoxymethyloxymethyl-3-cephem-4-carboxylate and 2,2,2-trichloroethyl d,l-7α-(p-nitrobenzyloxycarbonylamino)-3-methoxymethyloxymethyl-3-cephem-4-carboxylate To an ice-cold, stirring suspension of N-(p-nitrobenzyloxycarbonyl)-glycine (0.51 g, 2 mMol) in anhydrous ether (25 ml) is added phosphorus pentachloride (0.42 g, 2 mMol). After 30 minutes, 2,2,2-trichloroethyl 5-methoxymethyloxymethyl-6H-1,3-thiazine-4-carboxylate (0.70 g, 2 mMol) and triethylamine (1.01 g, 10 mMol) in anhydrous ether (25 ml) are added dropwise over 1 hour. The resulting mixture is washed with 5 portions of water. The second wash is acidified with pH 2 phosphate buffer and the fourth is basified with pH 9 phosphate buffer. The ethereal solution is dried with MgSO$_4$, filtered, and evaporated in vacuo. The residue is purified by chromatography on silica gel, affording 2,2,2-trichloroethyl d,l-7β-(p-nitrobenzyloxycarbonylamino)-3-methoxymethyloxymethyl-3-cephem-4-carboxylate and 2,2,2-trichloroethyl d,l-7α-(p-nitrobenzyloxycarbonylamino)-3-methoxymethyloxymethyl-3-cephem-4-carboxylate.

Step 2. 2,2,2-Trichloroethyl d,l-7β-amino-3-methoxymethyloxymethyl-3-cephem-4-carboxylate and 2,2,2-trichloroethyl d,l-7α-amino-3-methoxymethyloxymethyl-3-cephem-4-carboxylate A mixture of 2,2,2-trichloroethyl d,l-7-(p-nitrobenzyloxycarbonylamino)-3-methoxymethyloxymethyl-3-cephem-4-carboxylate (0.22 g, mixture of 7α- and 7β-isomers) and 10% palladium on powder charcoal (0.10 g) in methanol (10 ml) is hydrogenated at 40 psi. The catalyst is filtered off and the filtrate is evaporated in vacuo. Purification of the residue by preparative tlc gives 2,2,2-trichloroethyl d,l-7β-amino-3-methoxymethyloxymethyl-3-cephem-4-carboxylate and 2,2,2-trichloroethyl d,l-7α-amino-3-methoxymethyloxymethyl-3-cephem-4-carboxylate.

EXAMPLE 15

2,2,2-Trichloroethyl d,l-7β-amino-7-methoxy-3-methoxymethyloxymethyl-3-cephem-4-carboxylate Step 1. Methyl α-methoxyglycinate A mixture of methyl 2-azido-2-methoxyacetate (10.0 g), platinum oxide (0.50 g), and benzene (100 ml) is hydrogenated at 40 psi for 1 hour. The catalyst is removed by filtration through a pad of diatomaceous earth, and the filtrate is evaporated in vacuo to give methyl α-methoxyglycinate.

Step 2. Methyl N-(p-nitrobenzyloxycarbonyl)-α-methoxy-glycinate

Triethylamine (5.06 g, 0.05 mole) and p-nitrobenzyl chloroformate (10.78 g, 0.05 mole) are added to an ice-cold solution of methyl α-methoxyglycinate (6.10 g, 0.05 mole) in dry CH$_2$Cl$_2$ (100 ml). The resulting mixture is stirred in the cold and under N$_2$ for 2 hours, and then washed with 3 portions of water. The CH$_2$Cl$_2$ phase is dried over MgSO$_4$, filtered, and evaporated in vacuo. Recrystallization of the residue affords pure methyl N-(p-nitrobenzyloxycarbonyl)-α-methoxyglycinate.

Step 3. Sodium N-(p-nitrobenzyloxycarbonyl)-α-methoxyglycinate

Aqueous sodium hydroxide (10 ml of a 2.5 N solution) is added dropwise over 15 minutes to a stirring solution of methyl N-(p-nitrobenzyloxycarbonyl)-α-methoxyglycinate (7.46 g, 25 mMol) in methanol (5 ml). The methanol is removed under reduced pressure and the aqueous residue is lyophilized to give sodium N-(p-nitrobenzyloxycarbonyl)-α-methoxyglycinate.

Step 4. N-(p-Nitrobenzyloxycarbonyl)-α-methoxyglycyl chloride

Sodium N-(p-nitrobenzyloxycarbonyl)-α-methoxyglycinate (0.92 g, 3 mMol) is suspended in dry CH$_2$Cl$_2$ (25 ml) and cooled in an ice-water bath. Oxalyl chloride (0.38 g, 3 mMol) and 2 drops of pyridine are added. The resulting mixture is stirred in the cold for 2 hours, and then filtered. The filtrate, which contains N-(p-nitrobenzyloxycarbonyl)-α-methoxyglycyl chloride, is used directly in the next step.

Step 5. 2,2,2-Trichloroethyl d,l-7β-(p-nitrobenzyloxycarbonylamino)-7-methoxy-3-methoxymethyloxymethyl-3-cephem-4-carboxylate The N-(p-nitrobenzyloxycarbonyl)-α-methoxyglycyl chloride solution is added dropwise over 90 minutes to an ice-cold stirring mixture of triethylamine (0.30 g, 3 mMol) and 2,2,2-trichloroethyl 5-methoxymethyloxymethyl-6H-1,3-thiazine-4-carboxylate (0.70 g, 2 mMol) in dry CH$_2$Cl$_2$ (25 ml). The resulting solution is washed with four portions of water, dried over MgSO$_4$, filtered, and evaporated in vacuo to an oil. Chromatography of this material on silica gel affords 2,2,2-trichloroethyl d,l-7β-(p-nitrobenzyloxycarbonylamino)-7-methoxy-3-methoxymethyloxymethyl-3-cephem-4-carboxylate.

Step 6. 2,2,2-Trichloroethyl d,l-7β-amino-7-methoxy-3-methoxymethyloxymethyl-3-cephem-4-carboxylate 2,2,2-Trichloroethyl d,l-7β-(p-nitrobenzyloxycarbonylamino)-7-methoxy-3-methoxymethyloxymethyl-3-cephem-4-carboxylate (0.30 g) in dioxane (30 ml) is hydrogenated at 40 psi with 10% palladium on carbon (0.10 g.). The catalyst is removed by filtration and the filtrate is evaporated in vacuo to afford crude 2,2,2-trichloroethyl d,l-7β-amino-7-methoxy-3-methoxymethyloxymethyl-3-cephem-4-carboxylate.

EXAMPLE 16 p-Nitrobenzyl d,l-7β-amino-3-methoxymethyl-3-cephem-4-carboxylate and p-nitrobenzyl d,l-7α-amino-3-methoxymethyl-3-cephem-4-carboxylate

Step 1. p-Nitrobenzyl d,l-7β-(p-methoxybenzyloxycarbonylamino)-3-methoxymethyl-3-cephem-4-carboxylate and p-nitrobenzyl d,l-7α-(p-methoxybenzyloxycarbonylamino)-3-methoxymethyl-3-cephem-4-carboxylate To a stirring suspension of N-(p-methoxybenzyloxycarbonyl)-glycine (0.49 g, 2mMol) and Et₃N (0.28 ml, 2 mMol) in anhydrous THF (20 ml) cooled to −10° (ice salt) is added dropwise isobutyl chloroformate (0.26 ml, 2 mMol). After stirring an additional 30 minutes in the cold, the mixture is treated dropwise over 2 hours with a solution of p-nitrobenzyl 5-methoxymethyl-6H-1,3-thiazine-4-carboxylate (0.48 g, 1.5mMol) and Et₃N (0.21 ml, 1.5mMol) in THF (10 ml). The reaction mixture is stirred further at −10° for 2 hours and then it is allowed to warm to room temperature. The solvent is removed under reduced pressure and the residue is taken up in CH₂Cl₂, washed with water, dried over MgSO₄, and concentrated in vacuo. The crude produce is purified by chromatography on silica gel, affording p-nitrobenzyl d,l-7β-(p-methoxybenzyloxycarbonylamino)-3-methoxymethyl-3-cephem-4-carboxylate and p-nitrobenzyl d,l-7α-(p-methoxybenzylcarbonylamino)-3-methoxymethyl-3-cephem-4-carboxylate.

Step 2. p-Nitrobenzyl d,l-7β-amino-3-methoxymethyl-3-cephem-4-carboxylate and p-nitrobenzyl d,l-7α-amino-3-methoxymethyl-3-cephem-4-carboxylate.

A suspension of p-nitrobenzyl d,l-7α-(p-methoxybenzyloxycarbonylamino)-3-methoxymethyl-3-cephem-4-carboxylate (0.27 g, 0.5 mMol) in anisole (1.2 ml) is cooled to 0° and treated with ice-cold trifluoroacetic acid (6 ml). The resulting solution is kept at 0° for 5 minutes, after which the trifluoroacetic acid is evaporated in vacuo. The residue is washed several times with ether and then taken up in EtOAc & neutralized with Et₃N. The EtOAc solution is washed with water and brine, dried with MgSO₄, filtered, and evaporated in vacuo to afford p-nitrobenzyl d,l-7α-amino-3-methoxymethyl-3-cephem-4-carboxylate.

p-Nitrobenzyl d,l-7β-amino-3-methoxymethyl-3-cephem-4-carboxylate is obtained in the same way by de-blocking p-nitrobenzyl d,l-7β-(p-methoxybenzyloxycarbonylamino)-3-methoxymethyl-3-cephem-4-carboxylate.

EXAMPLE 17 p-Methoxybenzyl d,l-7β-amino-3-(N,N-di-p-methoxybenzyl)-carbamoyloxymethyl-3-cephem-4-carboxylate and p-methoxybenzyl d,l-7α-amino-3-(N,N-di-p-methoxybenzyl)carbamoyloxymethyl-3-cephem-4-carboxylate

Step 1. N-(2,2,2-trichloroethyloxycarbonyl)-glycyl trifluoromethanesulfonate A solution of N-(2,2,2-trichloroethyloxycarbonyl)-glycyl chloride (0.80 g, 3 mMol) in CH₂Cl₂ (30 ml) is prepared as described in Example 18, Step 2. This solution is cooled to 0° and treated with silver trifluoromethylsulfonate (0.77 g, 3 mMol). The mixture is stirred for 2 minutes, during which time silver chloride rapidly precipitates out. The mixture is filtered and the filtrate containing N-(2,2,2-trichloroethyloxycarbonyl)-glycyl trifluoromethanesulfonate is used immediately as described below.

Step 2. p-Methoxybenzyl d,l-7β-(2,2,2-trichloroethyloxycarbonylamino)-3-(N,N-di-p-methoxybenzyl)carbamoyloxymethyl-3-cephem-4-carboxylate and p-methoxybenzyl d,l-7α-(2,2,2-trichloroethyloxycarbonylamino)-3-(N,N-di-p-methoxybenzyl)carbamoyloxymethyl-3-cephem-4-carboxylate p-Methoxybenzyl 5-(N,N-di-p-methoxybenzyl)carbamoyloxymethyl-6H-1,3-thiazine-4-carboxylate (1.15 g, 2 mMol) is dissolved in dry CH₂Cl₂ (20 ml) and cooled to 0°. Triethylamine (0.42 ml, 3 mMol) is added and the mixture is treated dropwise over 2 hours with the solution of N-(2,2,2-trichloroethyloxycarbonyl)-glycyl trifluoromethanesulfonate. The reaction mixture is washed with pH 7 buffer, dried with MgSO₄, filtered, and evaporated in vacuo to a residue which is purified by chromatography on silica gel to give p-methoxybenzyl d,l-7β-(2,2,2-trichloroethyloxycarbonylamino)-3-(N,N-di-p-methoxybenzyl)carbamoyloxymethyl-3-cephem-4-carboxylate and p-methoxybenzyl d,l-7α-(2,2,2-trichlorethyloxycarbonyl)-3-(N,N-di-p-methoxybenzyl) carbamoyloxymethyl-3-cepham-4-carboxylate.

Step 3. p-Methoxybenzyl d,l-7β-amino-3-(N,N-di-p-methoxybenzyl)carbamoyloxymethyl-3-cephem-4-carboxylate and p-methoxybenzyl d,l-7α-amino-3-(N,N-di-p-methoxybenzyl)carbamoyloxymethyl-3-cephem-4-carboxylate Zinc dust (65 mg, 1 mMol) is added to a cold (ice-water bath), stirring solution of p-methoxybenzyl d,l-7β-(2,2,2-trichloroethyloxycarbonylamino)-3-(N,N-di-p-methoxybenzyl)carbamoyloxymethyl-3-cephem-4-p-methoxybenzyl)carbamoyloxymethyl-3-cephem-4-carboxylate (81 mg, 0.1 mMol) in 90% aqueous acetic acid (2 ml). The mixture is stirred vigorously for 45 minutes and then filtered to remove the zinc. The filtrate is evaporated in vacuo to a residue which is taken up in EtOAc. The solution is washed with water, dried over MgSO₄, and evaporated to yield p-methoxybenzyl d,l-7β-amino-3-(N,N-di-p-methoxybenzyl)carbamoyloxymethyl-3-cephem-4-carboxylate.

The 7α-amino compound is obtained in the same manner by starting with the 7α-(2,2,2-trichloroethyloxycarbonylamino) derivative.

EXAMPLE 18 p-Methoxybenzyl
d,l-7β-amino-3-acetoxymethyl-3-cephem-4-carboxylate
and p-methoxybenzyl
d,l-7α-amino-3-acetoxymethyl-3-cephem-4-carboxylate Step 1. N-(2,2,2-Trichloroethyloxycarbonyl)-glycine 2,2,2-Trichloroethyl chloroformate (23,30 g, 0.11 mole) and 4N NaOH (30 ml, 0.12 mole) are added alternately in about 5 equal portions over a period of 30 minutes to an ice-cold, vigorously stirring solution of glycine (7.51 g, 0.1 mole) in 4N NaOH (25 ml). Upon completion of the reaction, the solution is extracted with ether, and the aqueous portion is slurried with EtOAc and acidified in the cold to pH 2.5 with 6N HCl. The EtOAc solution is separated, washed with $H_2O$, dried over $MgSO_4$, filtered, and evaporated in vacuo to give N-(2,2,2-trichloroethyloxycarbonyl)-glycine.

Step 2. N-(2,2,2-Trichloroethyloxycarbonyl)-glycyl chloride

N-(2,2,2-Trichloroethyloxycarbonyl)-glycine (0.75 g, 3 mMol) is suspended in $CH_2Cl_2$ (30 ml) and the mixture is stirred under $N_2$ with ice-bath cooling. Oxalyl chloride (0.28 ml, 3.3 mMol) and DMF (0.023 ml, 0.3 mMol) are added thereto, and the mixture is stirred for 1 hour in the cold. The resulting solution is washed with ice-cold water and ice-cold brine, dried briefly over $Na_2SO_4$, and filtered. This solution of N-(2,2,2-trichloroethyloxycarbonyl)glycyl chloride is used immediately in the next step.

Step 3. p-Methoxybenzyl
d,l-7β-(2,2,2-trichloroethyloxycarbonylamino)-3-acetoxymethyl-3-cephem-4-carboxylate and
p-methoxybenzyl
d,l-7α-(2,2,2-trichloroethyloxycarbonylamino)-3-acetoxymethyl-3-cephem-4-carboxylate The $CH_2Cl_2$ solution of N-(2,2,2-trichloroethyloxycarbonyl)-glycyl chloride prepared in step 2 is added dropwise over 90 minutes to an ice-cold, stirring solution of p-methoxybenzyl 5-acetoxymethyl-6H-1,3-thiazine-4-carboxylate (0.67 g, 2 mMol) and $Et_3N$ (0.42 ml, 3 mMol) in dry $CH_2Cl_2$ (20 ml). After stirring an additional 30 minutes in the cold, the reaction mixture is washed with 5 portions of water. The second wash is acidified with pH 3 phosphate buffer and the fourth is basified with pH 9 phosphate buffer. The $CH_2Cl_2$ phase is dried with $MgSO_4$, filtered, and concentrated in vacuo to an oil. Chromatography of this material over silica gel affords p-methoxybenzyl d,l-7β-(2,2,2-trichloroethyloxycarabonylamino)-3-acetoxymethyl-3-cephem-4-carboxylate and p-methoxybenzyl d,l-7α-(2,2,2-trichloroethyloxycarbonylamino)-3-acetoxyemthyl-3-cephem-4-carboxylate.

Step 4. p-Methoxybenzyl
d,l-7β-amino-3-acetoxymethyl-3-cephem-4-carboxylate
and p-methoxybenzyl
d,l-7α-amino-3-acetoxymethyl-3-cephem-4-carboxylate p-Methoxybenzyl d,l-7β-(2,2,2-trichloroethyloxycarbonylamino)-3-acetoxymethyl-3-cephem-4-carboxylate (0.25 g) is dissolved in 90% aqueous acetic acid (10 ml). The solution is cooled in an ice-water bath. Zinc dust (0.50 g) is added and the mixture is stirred for 40 minutes. The zinc is filtered and washed with acetic acid. The filtrate and wash are combined and evaporated in vacuo, azeotroping with benzene to remove last traces of acetic acid. The residue is taken up in EtOAc, washed with water and saturated brine, dried with $MgSO_4$, filtered, and evaporated to afford p-methoxybenzyl d,l-7β-amino-3-acetoxymethyl-3-cephem-4-carboxylate.

In the same manner, p-methoxybenzyl d,l-7α-(2,2,2-trichloroethyloxycarbonylamino)-3-acetoxymethyl-3-cephem-4-carboxylate affords the corresponding 7α-amino derivative.

EXAMPLE 19 p-Methoxybenzyl
7-methylthio-7-(2-thienylacetamido)cephalosporanate

A. 2-Thiopheneacetamidoglycolic acid

A mixture of 1.4 g thiopheneacetamide, 1 g glyoxyic acid, 10 ml THF and 1 g powdered molecular sieves is stirred 4 days, filtered and evaporated. The residue is taken up in EtOAc, washed twice with sat. aq NaCl, dried with $MgSO_4$, filtered and evaporated to afford 2-Thiopheneacetamidoglycolic acid which is purified by chromatography on silica gel, eluting with 4:1:1 benzene-AcOH-MeOH. NMR (5, DMSO): 3.66s, $CH_2C=O$; 5.27d, J=9, C$\underline{H}$COOH; 6.9m, 7.3m, $C_4H_3S$; 8.75d, J=9, NH.

B. 2-Thiopheneacetamido-methylthioacetic acid

A mixture of 50 mg cpd I, one-half ml TFA and a few drops methanethiol is stirred 2 hrs at 25° and evaporated, affording 2-Thiopheneacetamido-methylthioacetic acid. NMR (5, DMSO): 2.10s, $SCH_3$; 5.17d, J=9, C$\underline{H}$COOH; 8.8d, J=9, NH; other peaks correct.

C. 2-Thiopheneacetamido-methylthioacetic acid, isobutyl carbonic anhydride

To 1 g 2-Thiopheneacetamido-methylthioacetic acid in 15 ml $CH_2Cl_2$ is added 1 equivalent $Et_3N$, and then, at 0° over 5 min, 1 equivalent isobutyl chloroformate, forming 2-Thiopheneacetamido-methylthioacetic acid, isobutyl carbonic anhydride.

D. p-methoxybenzyl
7-methylthio-7-(2-thienylacetamido cephalosporanate

To this solution at −78° is added p-methoxybenzyl 5-acetoxymethyl 6H-1,3-thiazine-4-carboxylate and then a second millimole of triethylamine. The reaction mixture is allowed to warm to room temperature over one hour, and kept at 25° one hour. The mixture is then washed successively with aqueous pH 2 buffer, water, and aqueous bicarbonate, dried with $MgSO_4$, filtered and evaporated, affording p-methoxybenzyl 7-methylthio-7-(2-thienylacetamido)cephalosporanate which may be purified if desired by chromatography on silica gel, eluting with 4:1 chloroform-ethyl acetate.

When other representative thiazines are used in place of methoxybenzyl 5-acetoxymethyl 6H-1,3-thiazine 4-carboxylate in the above process the corresponding cephalosporin is obtained. For example, when the following thiazines are employed: methyl 5-methyl-6H-1,3-thiazine-4-carboxylate, 2,2,2-trichloroethyl 5-benzyloxymethyl-6H-1,3-thiazine-4-carboxylate, p-methoxybenzyl 5-carbamoyloxymethyl-6H-1,3-thiazine-4-carboxylate, methoxymethyl 5-isobutryloxymethyl-6H-1,3-thiazine-4-carboxylate, p-methoxybenzyl-5-(N,N-di-p-methoxybenzyl)-carbamoyloxymethyl-6H-1, 3-thiazine-4-carboxylate and p-methoxybenzyl 5-(N-2,2,2-trichloroethyl)-carbamoyloxymethyl-6H-1,3-thiazine-4-carboxylate.

The following cephalosporins are obtained: methyl 7-methylthio 7-(2-thienylacetamido)-3-methyl decephalosporanate; 2,2,2-trichloroethyl 7-methylthio 7-(2-thienylacetamido)-3-benzyloxymethyl-3-cephem-4-carboxylate; p-methoxybenzyl-7-methylthio-7-(2-thienylacetamido)-3-carbamoyloxymethyl-3-cepham-4-carboxylate; methoxymethyl 7-methylthio 7-(2-thienylacetamido)-3-isobutryloxymethyl-3-cephem-4-carboxylate; p-methoxybenzyl 7-methylthio 7-(2-thienylacetamido)-3-N,N-di-p-methoxybenzyl-carbamoyloxymethyl-3-cephem-4-carboxylate and p-methoxybenzyl 7-methylthio 7-(2-thienylacetamido)-3-(N-2,2,2-trichloroethyl)-carbamoyloxymethyl-3-cephem-4-carboxylate.

The cephalosporins that are prepared in accordance with the invention are known valuable antibiotics active against various gram-positive and gram-negative bacteria and, accordingly, find utility in human and veterinary medicine. The known useful cephalosporin compounds can therefore be used as antibacterial drugs for treating infections caused by gram-positive or gram-negative bacteria and, accordingly, find utility in human and veterinary medicine. The known useful cephalosporin compounds can therefore be used as antibacterial drugs for treating infections caused by gram-positive or gram-negative bacteria, for example against *Staphylococcus aureus* (penicillin resistant), *Escherichia coli, Klebsiella pneumoniae, Salmonella typhosa, Pseudomonas* and *Bacterium proteus*. The antibacterial cephalosporins may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The cephalosporin products prepared in accordance with the process of the invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup acacia, gelatin, sorbitol, tragacanth, or polyvinylpyrrolidone; fillers, for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution emulsions, syrups, elixirs, etc. or may be presented as a dry product, for reconstitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible fats; emulsifying agents, for example lecithin, sorbitan monooleate or acacia; non-aqueous vehicles which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops, etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight. The preferred daily dosage for the compounds of the invention range from about 80 to 120 mg of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10 – 60%. The composition will generally contain from about 15 mg. to about 1500 mg. by weight of the active ingredient based upon the total weight of the composition; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

What is claimed is:

1. A process of producing useful cephalosporin antibiotics of the formula:

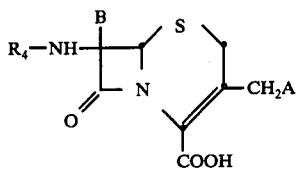

wherein B is H, CH$_3$, OCH$_3$ or SR' wherein R' is lower alkyl of 1–6 carbon atoms or phenyl;

R$_4$ is the acyl group of a carboxylic acylating agent capable of acylating the 7-amino group of a cephalosporin;

A is hydrogen, azido, halo, cyano, pyridinium, methylpyridinium, halopyridinium, carbamoylpyridiminium, N-hydroxymethylcarbamoylpyridinium, (N-carbomethoxycarbamoyl)pyridinium, (N-cyanocarbamoyl)pyridinium, (carboxymethyl)pyridinium, (hydroxymethyl)pyridinium, (trifluoromethyl)pyridinium, quinolinium, picolinium, lutidinium, hydroxy, carbamoyloxy, N-loweralkyl carbamoyloxy, N,N-diloweralkyl carbamoyloxy, a heterocyclic tertiary amine wherein the heterocycle is 5- or 6-membered and contains one or more nitrogen, oxygen or sulfur atoms, amino, aminomethyl, acetamidomethyl, carbamoylaminomethyl, 5-cyano-triazol-1-ylmethyl, 4-methoxycarbonyltriazol-1-ylmethyl, mercapto, alkylthio of 1–6 carbon atoms, lower alkanoyloxy, benzoyloxy, (p-chlorobenzoyl)oxy, (p-methylbenzoyl)oxy, furoyloxy, tosyloxy, 1-naphthoyloxy, or a 5-membered monocyclic heterocyclic thio radical having 1–4 nitrogen, oxygen or sulfur atoms; which comprises the cycloaddition of a glycine derivative of the formula

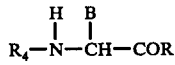

wherein R$_4$ and B have the same meaning as above and R is OH, halogen, O—COOR$_6$, or trifluoromethanesulfonate, CN, N$_3$ or OCOCF$_3$; with a thiazine derivative of the formula:

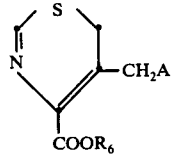

wherein A' is hydrogen, azido, halo, cyano, pyridinium, methylpyridinium, halopyridinium, carbamoylpyridinium, N-hydroxymethylcarbamoylpyridinium, (N-carbomethoxycarbamoyl)pyridinium, (N-cyanocarbamoyl)pyridinium, (carboxymethyl)pyridinium, (hydroxymethyl)pyridinium, (trifluoromethyl)pyridinium, quinolinium, picolinium, lutidinium, protected hydroxy wherein the protecting group is removable by mild aqueous hydrolysis or by hydrogenation, carbamoyloxy, N-loweralkyl carbamoyloxy, N,N-diloweralkyl carbamoyloxy, a heterocyclic tertiary amine wherein the heterocycle is 5-or 6-membered and contains one or more nitrogen, oxygen or sulfur atoms, protected amino, aminomethyl, acetamidomethyl, carbamoylaminomethyl, N,N-dimethylaminomethyl, N-(2-chloroethyl)aminomethyl, 5-cyano-triazol-1-ylmethyl, 4-methoxycarbamoyltriazol-1-ylmethyl, protected mercapto wherein the protecting group is removable by mild aqueous hydrolysis or by hydrogenation, alkylthio of 1–6 carbon atoms, lower alkanoyloxy, benzoyloxy, (p-chlorobenzoyl)oxy, (p-methylbenzoyl)oxy, furoyloxy, tosyloxy, p-tolylsulfonylthio, 1-naphthoyloxy or a 5-membered monocyclic heterocyclic thio radical having 1–4 nitrogen, oxygen or sulfur atoms;

R$_6$ is a carboxy protecting group wherein the protecting group is removable without disruption of the β-lactam group of the cephalosporin molecule; followed by removal of any protecting group at the A' or R$_6$ position.

2. A process according to claim 1 wherein the glycine derivative is of the formula:

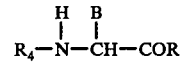

wherein R$_4$ is phenylacetyl, phenoxyacetyl, 3-bromophenylacetyl, p-aminomethylphenylacetyl, 4-carboxylmethylphenylacetyl, 4-carboxamidomethylphenylacetyl, 2-furylacetyl, 5-nitrofurylacetyl, 3-furylacetyl, 2-thienylacetyl, 5-chlorothienylacetyl, 5-methoxythienylacetyl, α-guanidino-2-thienylacetyl, 3-thienylacetyl, 4-methylthienylacetyl, 3-isothiazolylacetyl, 4-methoxyisothiazolylacetyl, 4-isothiazolylacetyl, 3-methylisothiazolylacetyl, 5-isothiazolylacetyl, 3-chloroisothiazolylacetyl, 3-methyl-1,2,5-oxadiazolylacetyl, 1,2,5-thiadiazolyl-4-acetyl, 3-methyl-1,2,5-thiadiazolyl-4-acetyl, 3-chloro-1,2,5-thiadiazolyl-4-acetyl, 3-methoxy-1,2,5-thiadiazolyl-4-acetyl, phenylthioacetyl, 4-pyridylthioacetyl, cyanoacetyl, tetrazolylacetyl, α-fluorophenylacetyl, D-phenylglycyl, 3-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-sulfaminophenylacetyl, α-hydroxyphenylacetyl, α-tetrazolylphenylacetyl and α-sulfophenylacetyl.

* * * * *